(12) United States Patent
Nagy

(10) Patent No.: US 12,385,873 B2
(45) Date of Patent: Aug. 12, 2025

(54) DETECTION OF TARGET NUCLEIC ACID MOLECULES

(71) Applicant: Aurangzeb Nafees Nagy, Las Vegas, NV (US)

(72) Inventor: Aurangzeb Nafees Nagy, Las Vegas, NV (US)

( * ) Notice: Subject to any disclaimer, the term of this patent is extended or adjusted under 35 U.S.C. 154(b) by 901 days.

(21) Appl. No.: 17/561,921

(22) Filed: Dec. 24, 2021

(65) Prior Publication Data

US 2022/0205945 A1    Jun. 30, 2022

Related U.S. Application Data

(60) Provisional application No. 63/163,527, filed on Mar. 19, 2021, provisional application No. 63/130,634, filed on Dec. 25, 2020.

(51) Int. Cl.
*G01N 27/327* (2006.01)
*C12Q 1/6813* (2018.01)

(52) U.S. Cl.
CPC .............................. *G01N 27/3276* (2013.01)

(58) Field of Classification Search
CPC ............ C12Q 1/6825; C12Q 2565/519; C12Q 2565/607; C12Q 2565/629; G01N 27/3276
See application file for complete search history.

(56) References Cited

U.S. PATENT DOCUMENTS

| | | | |
|---|---|---|---|
| 5,728,532 A | 3/1998 | Ackley | |
| 6,060,023 A | 5/2000 | Maracas | |
| 6,399,303 B1 | 6/2002 | Connolly | |
| 6,706,473 B1 | 3/2004 | Edman et al. | |
| 7,118,861 B1 | 10/2006 | Naaman et al. | |

(Continued)

FOREIGN PATENT DOCUMENTS

| | | | |
|---|---|---|---|
| DE | 4303446 A1 | 8/1994 | |
| WO | 2004010103 A2 | 1/2004 | |

(Continued)

OTHER PUBLICATIONS

Ahmad, M., Mustafa, F., Lizna, A., Rizvi, T.; Virus detection and quantification using electrical parameters; Scientific Reports, Oct. 30, 2014; DOI: 10.1038/srep06831.

(Continued)

*Primary Examiner* — Gurpreet Kaur
(74) *Attorney, Agent, or Firm* — Connie R. Masters

(57) ABSTRACT

The present invention relates to a test apparatus, system, and method of detecting target nucleic acid molecules in a biological fluid test sample through analyzing changes in electrical parameters caused by hybridization of target nucleic acids that are complementary to the at least partially single-stranded nucleic acid template strand portion of the probe. A test disc encloses at least one set of electrically separated electrodes with the probe bridging the electrodes. The test sample, potentially containing a target virus, is introduced into a cartridge well, and the test disc is added to the well under conditions permitting hybridization. Electrical parameters within the circuit are measured to detect the presence and concentration of any hybridization complexes formed. Multiple test disc structures, including a cylindrical configuration and a cone construct, are disclosed.

13 Claims, 18 Drawing Sheets

(56) References Cited

U.S. PATENT DOCUMENTS

| | | | |
|---|---|---|---|
| 7,384,749 | B2 | 6/2008 | Kayyem et al. |
| 8,078,408 | B2 | 12/2011 | Albert et al. |
| 9,598,722 | B2 | 3/2017 | Wright et al. |
| 10,386,338 | B2 | 8/2019 | Wright |
| 10,670,559 | B2 | 6/2020 | Mannion et al. |
| 2004/0023253 | A1 | 2/2004 | Kunwar et al. |
| 2005/0053996 | A1* | 3/2005 | Tong .............. C12Q 1/6825 |
| | | | 435/6.16 |
| 2007/0184446 | A1 | 8/2007 | Matsumoto et al. |
| 2011/0227558 | A1 | 9/2011 | Mannion et al. |
| 2017/0121761 | A1 | 5/2017 | Eichen et al. |
| 2018/0095081 | A1 | 4/2018 | Albert et al. |
| 2019/0094175 | A1 | 3/2019 | Merriman et al. |
| 2020/0002758 | A1 | 1/2020 | Moon |
| 2020/0165667 | A1 | 5/2020 | Steinmüller-Nethl et al. |

FOREIGN PATENT DOCUMENTS

| | | |
|---|---|---|
| WO | 2005019413 A2 | 3/2005 |
| WO | 2013127244 A1 | 9/2013 |
| WO | 2016160877 A1 | 10/2016 |
| WO | 2017205827 A1 | 11/2017 |
| WO | 2020132005 A1 | 6/2020 |

OTHER PUBLICATIONS

International Search Report dated Jun. 8, 2022 for International Application No. PCTUS2021065182 filed on Dec. 24, 2021.

Kassegne et al. Numerical modeling of transport and accumulation of DNA on electronically active biochips. Sensors and Actuators B. Aug. 15, 2003, vol. 94, No. 1.

Liu et al. Fabrication of ZnO Nanowire Field-Emitter Arrays With Focusing Capability. IEEE Transactions on Electron Devices. May 2018, vol. 65, No. 5.

Written Opinion of International Search Authority dated Jun. 8, 2022 for International Application No. PCTUS2021065182 filed on Dec. 24, 2021.

Yang et al. An immunoassay cassette with a handheld reader for HIV urine testing in point-of-care diagnostics. Biomedical Microdevices. May 21, 2020, vol. 22, No. 39.

Zaffino et al. Nanoprobes for enhanced electrochemical DNA sensors. Advanced Review. Wiley Interdisciplinary Reviews: Nanomedicine and Nanobiotechnology. Nov.-Dec. 2015, vol. 7, No. 6.

* cited by examiner

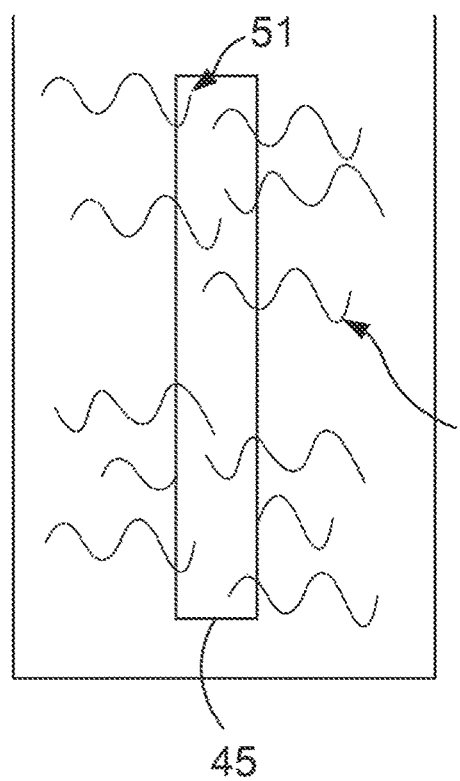
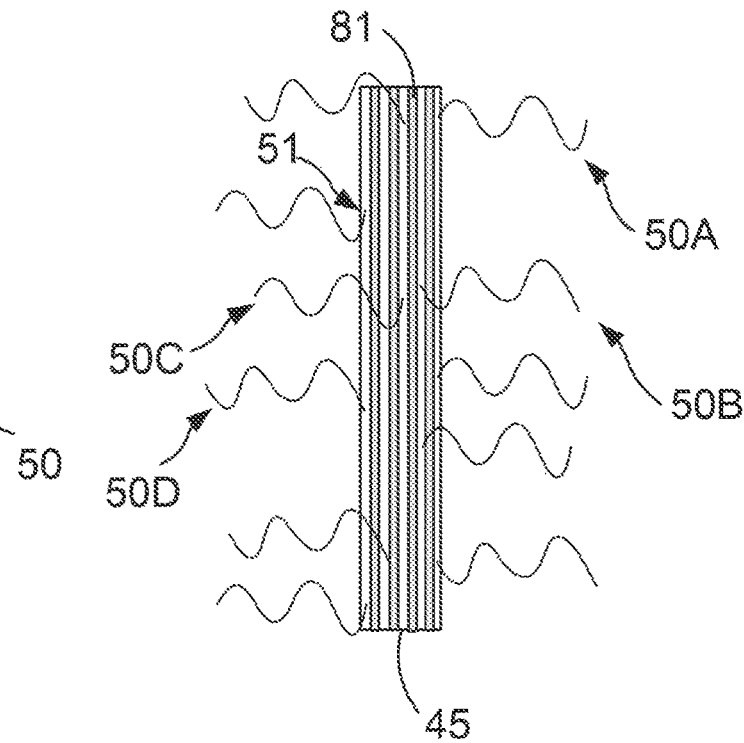
FIG. 15    FIG. 16
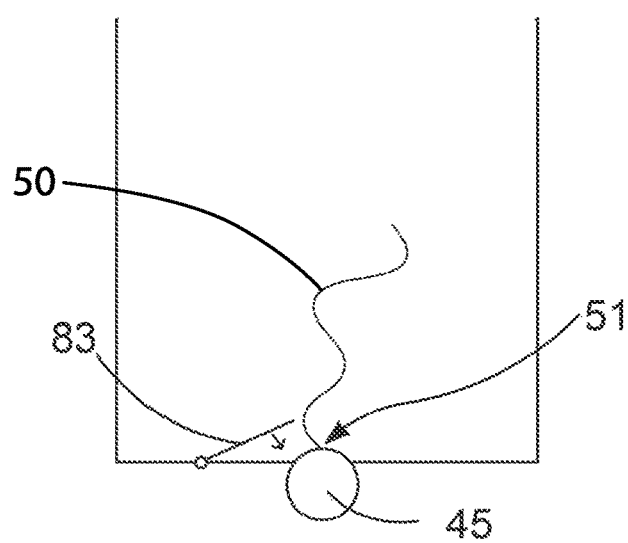
FIG. 17

DETECTION OF TARGET NUCLEIC ACID MOLECULES

FIELD OF INVENTION

This invention relates generally to the field of molecular biology. More specifically, the invention relates to a rapid, label-free diagnostic biosensor test system to detect specific target nucleic acid sequences by using variations in electrical parameters occurring when target single-strand nucleic acid molecules from a biological fluid specimen hybridize with probe nucleic acid molecules in a test disc.

BACKGROUND OF THE INVENTION

The current COVID-19 pandemic, with its global economic impact and personal disruptive effect, has magnified the awareness of the value of, and need for, inexpensive-to-produce, economical-to-use, and easily configurable, rapid diagnostic tests for detecting viral ribonucleic acid (RNA), such as the pandemic's enveloped positive-sense single-stranded novel beta coronavirus SARS-CoV-2.

Hybridization may be used to detect the presence of a specific target RNA or deoxyribonucleic acid (DNA) sequence in a sample or specimen to be analyzed. Hybridization is based on the complementary binding of specific target single-stranded nucleic acid polymer molecules contained within a test specimen to single-stranded nucleic acid polymer molecules of a prepared probe. In a conventional hybridization test, the probes are labeled, the target viral nucleic acid molecules are amplified, hybridization is allowed to occur, and the label is detected by autoradiography, fluorescence, or color or light forming reactions.

A widely used method that uses hybridization to detect viral RNA is the reverse transcriptase polymerase chain reaction (RT-PCR) in which a mucosal sample/specimen is typically obtained via a nasopharyngeal swab. The RNA of the test specimen is extracted, purified, reverse transcribed into complementary DNA, and amplified through thermal cycling. The complementary DNA strand is labeled for detection. But the multiple cycles of hybridization and nucleic acid synthesis along with the process of detecting the particular target nucleic acid of interest lengthens the time required to obtain a result. Also, due to the need for a fully equipped laboratory with technically skilled technicians, the possibility of contamination, and the high cost of each test, this method of detecting target nucleic acid polymers is not suitable for use in a rapid or point-of-care test. Additional amplification methods, such as loop mediated isothermal amplification (LAMP), nucleic acid sequence-based amplification (NASBA), strand displacement amplification (SDA), multiple displacement amplification (MDA), and ligase chain reaction (LGR) are also known, but they suffer from similar limitations of possible sample contamination, time-intensive amplification, and the need for expensive laboratory staff and equipment.

Nucleic acid microarrays, used for sequencing and diagnostic applications, are also known. A nucleic acid microarray includes a collection of binding sites each carrying a nucleic acid probe for recognizing specific target complementary nucleic acid sequences. A test specimen, potentially including one or more types of labeled single-stranded target nucleic acid, is introduced into the microarray, and any probe-to-target hybridization that occurs is detected via the labeling. This method provides the ability to distinguish between multiple pathogens, but the testing, which must be done in a fully equipped laboratory with highly trained staff to detect the labeling, is expensive and is not amenable to point-of-care administration.

Several methods have been proposed for using electrical measurements to detect hybridization including linear designs comprising two strips of metal used as electrodes. Some designs use precisely engineered nanofabricated, fluid-filled pores, such as described by Healy, K., B. Schiedt and A. Morrison, "Solid-state nanopore technologies for nanopore-based DNA analysis," *Nanomedicine* 2 6 (2007), pages 875-97. Nanofluidic channels have also been disclosed, such as in U.S. Pat. No. 10,670,559 issued to Mannion, et al., on Jun. 2, 2020. In that patent, molecules in solution are driven through the nanofluidic channels, which contact a charge sensor (a nanowire, nanotube, transistor, or capacitor), with the altered electric potential induced by hybridization measured without labeling of the target. However, it is difficult to synthesize the nanowire in a precise location, which leads to inconsistencies in the structure and results. Also, the cost of the test is increased by the amount of metal required and the exactitude required in the nanofabrication of precise nanofluidic channels.

These and other proposed methods have failed to provide an accurate, inexpensive to produce, uncomplicated to administer, rapid, point-of-care test for detecting specific nucleic acid sequences that does not require labeling, thermal cycling, or amplification.

Accordingly, there is a need for a system, device, and method to detect specific target nucleic acid sequences rapidly, accurately, reliably, sensitively, and economically for diagnostic and other purposes, which can be used at the point of care and does not require the use of labels, amplification, or thermal cycling.

BRIEF SUMMARY OF THE INVENTION

The present invention is directed to a rapid test apparatus, system, and method for detecting the presence, concentration, and/or identity of target single-strand nucleic acid (ssNA) polymeric molecules present within a biological fluid specimen without the use of labels or thermal cycling and without requiring amplification of the target nucleic acid molecules. This is accomplished through sensing changes in electrical parameters, which occur due to hybridization of target ssNA biomolecules with probe single-stranded or partially single-stranded nucleic acid (ss/pssNA) molecules that are at least partially complementary to the target ssNA biomolecules. The probe ss/pssNA molecules bridge a gap between two spaced-apart conductors/electrodes housed within a disposable test disc, which is designed to be received into a test cartridge. If target ssNA molecules are present in the specimen, hybridization occurs, and double-stranded hybridized complexes are created. The electrical sensing device detects the difference in electrical parameters (conductivity, resistance, and the like) among double-stranded nucleic acid (dsNA) hybridized complexes, partially dsNA hybridized complexes, and unhybridized probe ss/pssNA molecules. These values are used to analyze the presence or absence and/or concentration of the target ssNA within the specimen based on the degree of hybridization. The presence or degree of hybridization may be based on known electrical parameter changes, such as, for example, the higher rate of conductivity and lower resistance of dsNA compared to ssNA.

The presented test apparatus, test system, and test method are suited for detection of both target single-strand DNA (ssDNA) molecules (such as for testing for genetic defects)

or target single-strand RNA (ssRNA) molecules (such as for testing of bodily fluids for virus infection). The disclosed test apparatus, system, and method may additionally be used for environmental testing of samples to determine contamination. In a disclosed exemplary embodiment, the test apparatus, system, and method, are directed to point-of-care rapid testing of bodily fluids potentially containing a viral load.

In one aspect the probe nucleic acid molecules are single-stranded RNA (ssRNA). In another aspect the probe nucleic acid molecules are partially single-stranded ribonucleic acid molecules (pssRNA). In a further aspect the probe nucleic acid molecules are single-strand DNA (ssDNA). In an additional aspect the probe nucleic acid molecules are partially single-stranded DNA molecules (pssDNA). In another aspect of the invention, the probe nucleic acid molecules comprise single-strand or partially single-strand peptide nucleic acid molecules (PNA), which may provide an advantage because of the affinity and specificity with which they hybridize with target nucleic acid molecules. Thus, whether the target nucleic acid molecules are ssDNA molecules or ssRNA molecules, they may be detected using ss/pssNA probes, such as ssDNA, pssDNA, ssRNA, pssRNA, ssPNA, or ssPNA.

The probe includes at least a center template portion of nucleic acid molecules comprising a nucleic acid sequence that is complementary to the nucleic acid sequence of the target (or at least a portion of the target sequence) of interest. The probe may also include tail and head portions attached to the center portion template strand that are not complementary to the target, but that may serve to attach (or attract) the probe to the electrodes within a test disc or to lengthen the probe.

Though the invention is applicable to other applications, the exemplary application described herein provides detection of the presence and concentration of viral ribonucleic acid (RNA), such as found in the novel coronavirus SARS-CoV-2. In this example, the template portion of the probe ss/pssNA molecules are synthesized to be complementary to, and to hybridize with, target ssRNA molecules of the novel coronavirus of the current pandemic.

The test apparatus includes a cartridge and a disposable disc. The cartridge is configured with a specimen-receiving aperture on its upper surface that receives the biological fluid to be tested, and, in the preferred aspect of the invention, also serves as a disc-receiving aperture that accommodates the disc. The disc has an outer housing enclosing a disc test chamber. Disposed within the test chamber is a first conductor (electrode) and a second conductor (electrode) with at least one (and typically many) probe ss/pssNA molecules bridging the gap between the two conductors. The head of the probe is attached to the first conductor, and the probe tail is attached to or attracted to the opposing second conductor.

In the first embodiment of the test disc, the disc's interior test chamber encloses two electrically separated conductors with the central first conductor disposed in the center of the disc and with the second conductor formed by the outer wall of the disc or by a wall-like cylindrical metallic border disposed inwardly of, and adjacent, to the disc outer wall. The second conductor/electrode can be coated chemically with a fixative that allows binding of the tail of the probe. Correspondingly, the metallic central first conductor can be chemically coated with a fixative that allows binding of the probe head.

In the second embodiment of the test disc, the disc includes an interior test chamber enclosing a truncated cone-shaped apparatus that incorporates the two electrically separated conductors. A metallic central first conductor is disposed at the top of the truncated cone and, as in the first embodiment, may be chemically coated with a fixative that allows binding of the head of the probe. A second conductor is disposed at a lower portion of the cone (extending upwardly from the circular plane surface of the cone base to the middle of the cone or below). An intermediary, non-conductive material is disposed at an in-between location, sandwiched between the two conductors and electrically separating them. Though a fixative to chemically coat the second electrode can be used, in a preferred aspect of the invention, no fixative is used. Instead, gravity and charge may serve to attract the probe tail to the second electrode.

The test system includes the cartridge (preferably disposable), the disposable test disc that will be received into the cartridge and that carries the electrodes with attached probe, and an electrical sensing subsystem. The electrical sensing subsystem includes a detection circuit for detecting electrical parameters and a signaling device that indicates the results of the detection circuit.

In an exemplary method of use, the test system includes introducing a sample biological fluid into a concave, specimen-receiving upper well of the cartridge, mixing the biological fluid with a reagent to open any viral agents contained within the biological fluid and to unwind the target ssRNA, introducing the test disc into the well, and allowing any target ssRNA molecules to hybridize with at least the template portion of the probe ss/pssNA molecules within the test disc. The cartridge with its installed disc is inserted into the electrical sensing subsystem. The sensing device, or "reader," reads the conductivity or resistance between the two electrodes, and the result is correlated to a predetermined array of conductivity and/or resistance values to determine the presence and/or concentration of the target ssRNA. In another aspect, the electrical sensing subsystem also supplies current to the two electrodes within the disc.

The method provides on-cartridge processing of biological fluids to provide an economical yet accurate analysis result. The low complexity allows administration at the point-of-care without the need for advanced laboratory equipment or highly skilled technicians.

The design of the test disc provides a reduction in the amount of material required as compared to current linear designs. This is because current linear designs require two strips of equal amounts of metal, whereas the central axial electrode requires less material overall. Also, the design uses less material while providing an equivalent testing volume, since the disclosed cylindrical design has a smaller perimeter than a rectangular or polygonal prism having equal volume.

The second embodiment of the test disc, which discloses the cone construction, eliminates the need to prepare the second electrode (disposed along the base of the cone and extending upwardly up to half the height of the cone) chemically. Instead, gravity and charge are relied upon to bring the probe's tail into close enough proximity to allow the tail to connect to the second electrode. Overall, this means that production of the test apparatus, which produces results equivalent or superior to the results of prior art devices can be achieve for a lower cost.

Another advantage of the test apparatus of the current invention over prior art devices is in the size. Due to the radial/cylindrical design, the height can be smaller than the prior art devices. Many of the linear designs rely on some amount of bowing of the probe and require some height to allow the sample biological fluid to bathe the prepared probe nucleic acid strands. The disclosed radial/cylindrical design allows the test apparatus (the cartridge including the installed disc) to be as flat as, and a similar size as, a credit card. This, in turn, could allow the electrical sensing device (i.e. the reader) to be as small as a cell phone.

Thus, the present invention provides rapid, low-cost, and accurate qualitative and/or quantitative analysis of test samples of biological fluid, while being small and inexpensive to manufacture.

The object of the invention is to provide a test apparatus, system, and method that detects the presence and concentration of a particular target sequence of nucleic acid molecules in a specimen without the use of labels and gives an improved performance over the above-described prior art devices, systems, and methods.

These and other objects, features, and advantages of the present invention will become more readily apparent from the attached drawings and from the detailed description of the preferred embodiments which follow.

BRIEF DESCRIPTION OF THE SEVERAL VIEWS OF THE DRAWINGS

The preferred embodiments of the invention will hereinafter be described in conjunction with the appended drawings, provided to illustrate and not to limit the invention, where like designations denote like elements.

FIG. 15 is a schematic side view of probe heads attached randomly to the first conductor in an embodiment of the present invention.

FIG. 16 is a schematic side view of probe heads attached in aligned rows to the first conductor in an embodiment of the present invention.

FIG. 17 is a schematic end view of the first conductor showing a means of depositing heads of probe nucleic acid molecules in an aligned row in an embodiment of the present invention.

Like reference numerals refer to like parts throughout the several views of the drawings.

DETAILED DESCRIPTION OF THE INVENTION

Figure 1A:
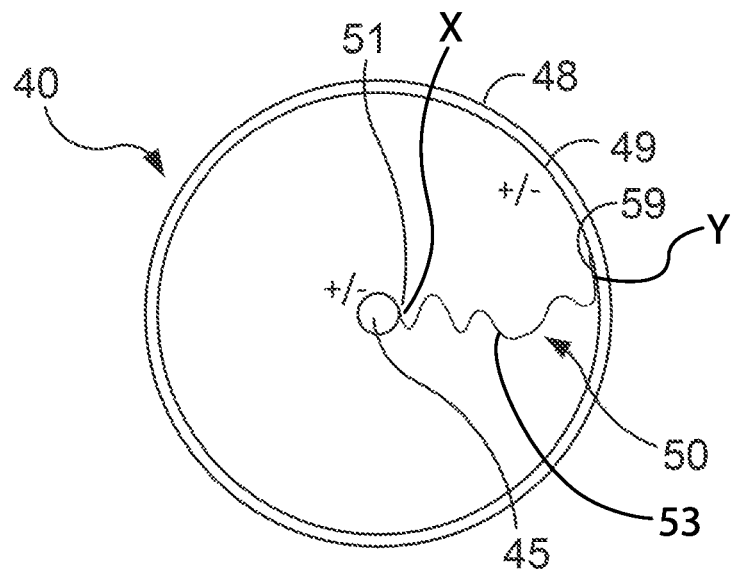
FIG. 1A is top view schematic of first embodiment of the test disc of the invention with a single-stranded or partially single stranded nucleic acid (ss/pssNA) probe bridging the gap between a first and second electrode in a test disc.

The present invention is directed toward a test apparatus ii (FIGS. 4C, 5C-D, 6C-6E, 11-13, 26C-26D), test system 10 (FIGS. 18, 19, 27-20), and test method for rapidly detecting the presence and/or concentration of target single-strand nucleic acid (ssNA) molecules 60 (FIGS. 1B, 5D, 6D, 25, 26D) within a specimen/sample of biological fluid 17 (FIGS. 4A, 5A, 6A, 7, 10, 26A), without the use of labeling, thermal cycling, or nucleic acid amplification. This is done by analyzing the change in one or more electrical parameters produced when hybridization or partial hybridization occurs between the target ssNA molecules 60 from the specimen 17 and the at least partially complementary probe nucleic acid molecules 50 (FIGS. 1A-1B, 4B-4C, 5B-5D, 6B-6E, 8, 10-25, 26B-26D, 27-29) spanning the gap between spaced conductors/electrodes 45, 49 (FIGS. 1A-1B, 4B-4C, 5B-5D, 6B-6E, 8, 10, 14, 20-25, 26B-26D, 27-29) held within an interior chamber of a test disc 40 (FIGS. 1A-1B, 4B-4C, 5B-5D, 6B-6E, 7-14, 18-19, 24-25, 26B-26D, 27-30).

The test apparatus ii comprises the test disc 40 and a cartridge 20 to receive the test disc 40. The test system 10 includes the test apparatus n and an electrical sensing subsystem 70 (FIGS. 18-19, 28-30). The electrical sensing subsystem 70 includes a detection circuit 71 (FIGS. 18-19, 28-30) for detecting electrical parameters and a signaling device 75 (FIGS. 18-19, 28-30) for indicating the results of the detection circuit 71.

Though the invention is suitable for use in detecting specific sequences of any nucleic acid, it is described herein in terms of an exemplary application for detecting viral ssRNA (such as the ssRNA of the novel SARS-CoV-2 coronavirus) within a sample biological fluid 17 (FIGS. 4A, 5A, 6A, 7, 10, 26A). And, though the invention may prove useful in sophisticated laboratories and with highly skilled technicians, it finds particular applicability in point-of-care rapid testing.

The test disc 40 includes an outer housing 48 with two electrically separated conductors 45, 49 disposed within the outer housing 48. Probe nucleic acid molecules 50 are created and are then installed within the outer housing. (Only one probe nucleic acid molecule 50 is shown in most figures for clarity of illustration, though, when in use, typically many probe nucleic acid molecules 50 would be included in each test disc 40.) The probe nucleic acid molecule 50 is a single-stranded or at least partially single-stranded nucleic acid (ss/pssNA) molecule that bridges the gap between the conductors 45, 49. In one aspect of the invention, the disc 40 further comprises a reagent compartment 30 (FIGS. 6B-6E).

Two arrangements of the first and second conductors 45, 49 are disclosed. A first embodiment of the test disc 40 provides a central/axial first conductor 45 and a perimeter second conductor 49 disposed at the outer wall of the test disc 40. The second embodiment of the test disc 40 provides a central/axial first conductor 45 disposed at a center top of a truncated cone and a second conductor 49 disposed at the wide base of the cone.

The test disc 40 may be formed in any of a variety of shapes. FIGS. 1A, 1B, 7, 9, 24-25, 28-29 illustrate a preferred cylindrical-shaped disc outer housing 48. In another aspect of the invention (FIGS. 18-19), the outer housing 48 forms an octagonal cylinder. In other aspects, the test disc 40 may be embodied in other shapes, such as in the shape of a cube, rectangular prism, or other polygonal prism.

The cartridge 20 includes a cartridge top portion, an opposing elongated bottom portion, and side portions. The width and length of the cartridge are based on considerations such as the ease and cost of manufacturing, the ability for the user to handle the cartridge, and the structure and supportiveness required to receive the disc 40. Though shown in the illustrations as a thin rectangular prism, other shapes may be used. The top surface of the cartridge 20 is configured with a concave depression forming a well 25. The well outer walls 21 and the well bottom floor 22 define the sides and bottom of an open-top space, the specimen-receiving aperture 29. In the variations shown, the specimen-receiving aperture 29 is defined by cylindrical walls, though the well 25 may take other shapes. For example, to receive the disc 40 of FIGS. 18-19, the well 25 could be octagonal. The well 25 is configured to have sufficient volume for receiving a sample biological fluid 17. In a preferred aspect of the invention, the specimen-receiving aperture 29 of the well 25 also serves as a disc-receiving aperture.

The biological fluid 17 comprises an environmental specimen or bodily fluid, such as saliva, nasal mucous, cerebrospinal fluid, blood, and the like. The sample or specimen of the biological fluid to be tested is introduced into the concave well 25. Though the biological fluid 17 is in the liquid state, the specimen need not be natively in the liquid state (such as blood or saliva), but a specimen may instead be obtained in a solid or partially solid state (such as a soil sample) that is suspended in fluid for testing.

Each probe ss/pssNA molecule 50 has a head 51 attached to the first electrode 45 and has a tail 59 attached to or attracted to the second electrode 49. In an aspect, the probe nucleic acid molecules 50 are not attached tautly but include an additional length of nucleic acid to allow a lax or slack architecture. In an aspect of the invention, the probe 50 is attached to the first and/or second electrode through use of one or two anchor strands of oligonucleotide sequences 57, as discussed in relation to FIGS. 20-23 below.

Figure 31:
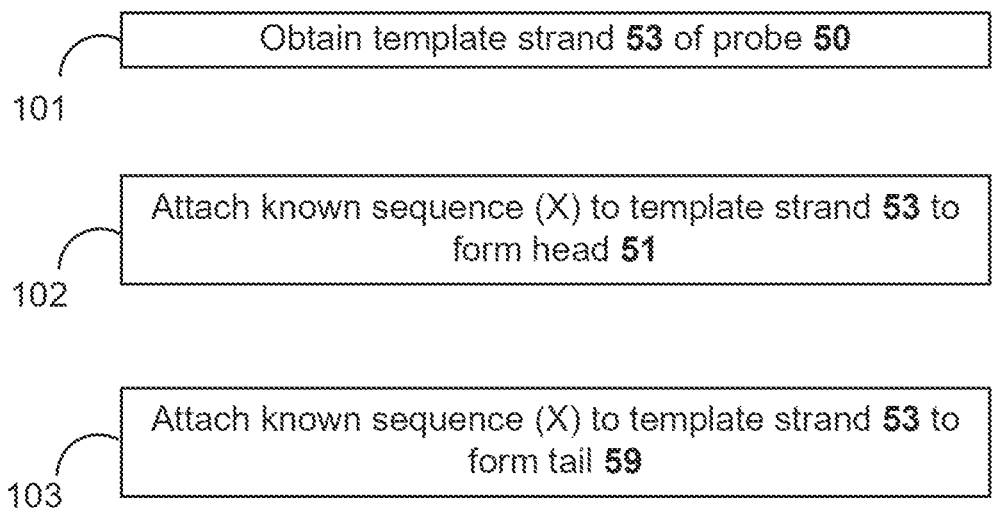
FIG. 31 is a flowchart showing steps in an exemplary preparation of the probe of the present invention.

The preparation of the probe 50 is described in the flowchart of FIG. 31. In this preferred aspect, the probe 50 includes a centrally disposed template portion 53 (FIGS. 1A, 20-24) that comprises a nucleic acid sequence that is complementary to the nucleic acid sequence of the target nucleic acid molecule of interest. This template portion 53 is obtained 101 (FIG. 31) from a vendor or synthesized. A first nucleic acid segment of known sequence (X) is enzymatically attached 102 (FIG. 31) to the 5' end of the template portion 53 to form the head 51. A second nucleic acid segment of known sequence (Y) is enzymatically attached 103 (FIG. 31) to the 3' end of the template portion 53 to form the tail 59. Optionally, the inverse orientation may be formed with the 5' end attached to the nucleic acid segment of known sequence (Y) to form the tail 59 and with the 3' end attached to the nucleic acid segment of known sequence (X) to form the head 51.

Figure 32:
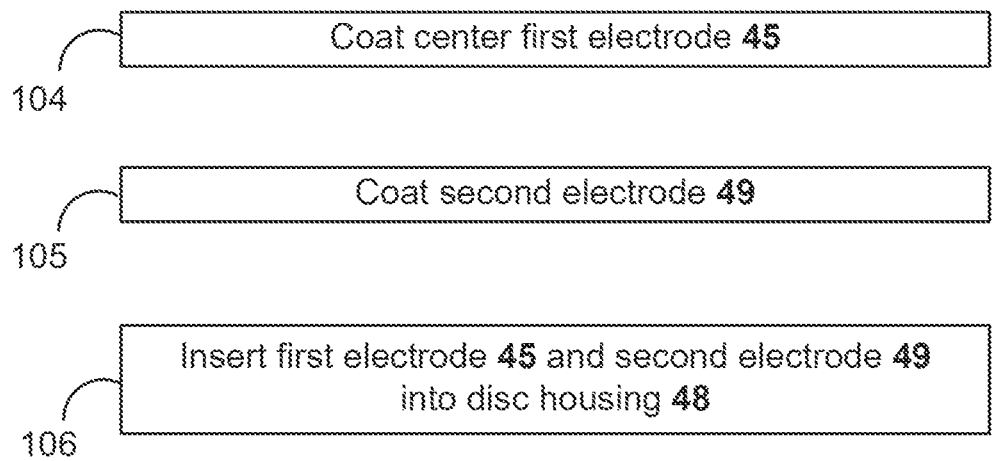
FIG. 32 is a flowchart showing steps in an exemplary preparation of the specimen-receiving disc before introduction of the probe of the present invention.

A preferred method of preparation of the electrodes 41, 49 of the test disc 40 of the first embodiment is shown in the flowchart of FIG. 32. In the first step 104, the metallic axial first electrode 45 is coated with a fixative that allows binding of the 5' end having the known sequence (X) to the axial first electrode 45. The second electrode 49 (which is a cylindrical metallic border to be positioned inside the outer wall of the disc 40 or which may comprise the outer wall of the disc 40) can be coated 105 chemically with a fixative that allows it to bind to the 3' end of known sequence (Y). The central first electrode 45 and the second electrode 48 are placed within the disc 40. In one aspect of the invention, shown in FIGS. 19, 29-30, the disc 40 is divided into multiple pie-shaped sections with radial dividers 39 disposed between the segments.

Figure 33:
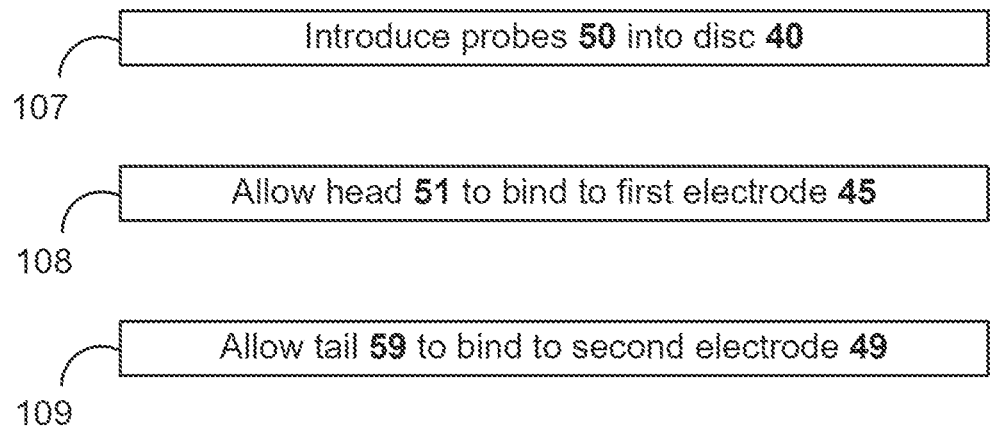
FIG. 33 is a flowchart showing steps of introducing the probe molecules into the test disc of the present invention.

The flowchart of FIG. 33 shows the final steps in preparing the disc. Multiple duplicates of the prepared probe nucleic acid strands 50 are introduced 107 into the disc. Then the known sequence (X) sections of the probe 50 bind 108 to the central electrode 45. Then known sequence (Y) sections of the probe 50 bind 109 to the second electrode 49. In the aspect in which the disc is separated into multiple pie-shaped segments, a first set of multiple duplicates of the prepare probes 50 can be placed into a first pie-shaped segment, and a second set can be placed into a second segment. More sets of types of prepared probes 50 can similarly be placed in additional segments. This allows for testing for more than one type of target 60 in a single disc.

Figure 34:
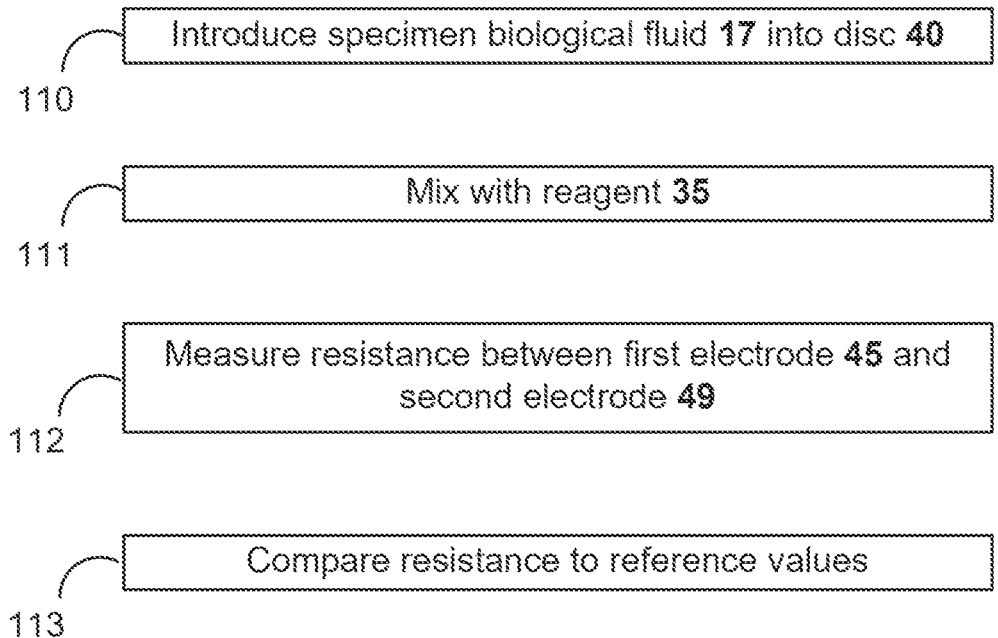
FIG. 34 is a flowchart showing steps of performing the rapid test to detect target nucleic acids of the present invention.

The flowchart of FIG. 34 gives a summary of the testing steps, after the probes 50 are in place in the disc 40. The specimen biological fluid 17 is introduced no into the disc 40. This generally includes introducing both the fluid 17 and the disc 40 into the well 25. The fluid 17 is mixed with the reagent 35. The electrical parameter (preferably resistance) is measured 112 between the first electrode 45 and the second electrode 49. The measured resistance value is compared 113 to stored values predetermined by testing to determine the presence of the target 60 via hybridization.

The electrical sensing subsystem 70 (FIGS. 18-19, 28-30 may include a voltmeter, an ammeter, or a functional equivalent thereof. The electrical sensing subsystem 70 analyzes one or more electrical parameters of the electrical circuit. The electrical sensing subsystem 70 may also supply to the test disc the current needed for the test. Sensing device 70 includes a detection circuit 71 for detecting the one or more electrical parameters and a signaling device 75 that indicates the results of the detection circuit to the technician. The signaling device 75 preferably includes a display screen. In one aspect of the invention, the display screen is integrated into the body of the electrical sensing subsystem 70. In another aspect of the invention, the display screen may be remote from the body of the electrical sensing subsystem 70. If the display screen is remote, the data from the detection circuit 71 may be transmitted by known wired or wireless methods. For example, the data may be transmitted wirelessly to a mobile phone/smartphone with the phone display screen used to display the data or may be transmitted via a wired connection to an adjacent display screen. Optionally, an audio alert may also be included in the signaling device 75.

Turning to the first embodiment of the test disc 40 in the schematic of FIG. 1A, the test disc 40 comprises the outer housing 48 including an outer cylindrical wall, a top side 41 (FIGS. 4B, 5B, 26B), and a bottom side 55 (FIGS. 4B, 5B, 26B) that enclose and define a disc interior test chamber. Within the interior chamber are two electrically separated conductors, the center first conductor 45 and the perimeter second conductor 49. Both the first conductor 45 and the second conductor 49 are configured to receive electrical current from a source. The electrical current may be supplied by a power source, such as a battery, within the cartridge 20, but it is preferred that the electrical current be supplied by the electrical sensing device 70 (FIGS. 18-19) to minimize the cost of the cartridge 20 and disc 40.

Figure 24:
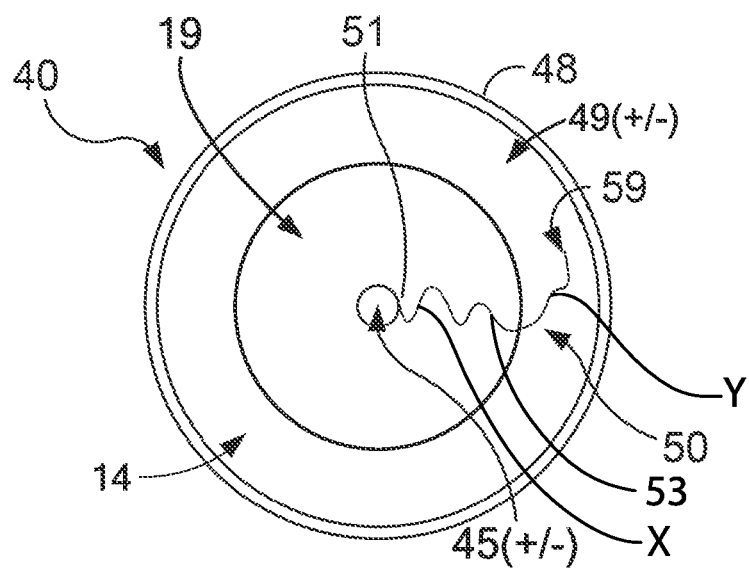
FIG. 24 is a schematic top view of a test disc of the second embodiment with the truncated cone construction inserted into the test disc.

As seen in a preferred aspect shown in the schematic of FIGS. 1A, 24, a longer tail 59 also provides an advantage in that the tail 59 is sufficiently long to trail along the second electrode 49. This laxity is enabled by an extra length of nucleic acids disposed at the tail 59 beyond the length required to stretch between the conductors 45, 49. This allows the tail 59 to remain near and attracted to (or attached to) the second conductor 49 even after contraction occurs during formation of the hybridization complex (FIG. 1B, 25) with a complementary target nucleic acid molecule. In this aspect, the tail 59 is configured with sufficient additional length that may be achieved by modification of the distal end of the tail 59 by the addition of adjunct molecules, which include non-complementary nucleic acid molecules such as garbage single-strand or double-strand RNA or garbage single-strand or double-strand DNA.

Figure 1B:
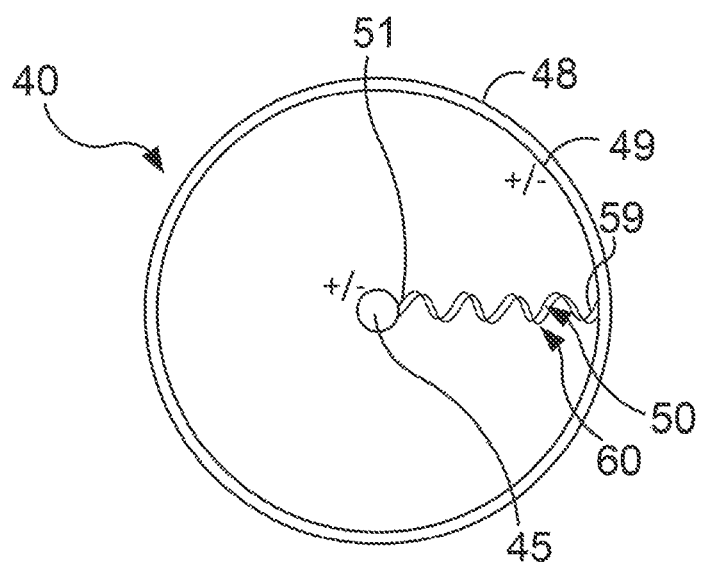
FIG. 1B is a top view schematic showing the test disc of FIG. 1A with a single-stranded nucleic acid (ssNA) molecule target hybridized with the ss/pssNA probe in a first embodiment of the present invention.
Figure 25:
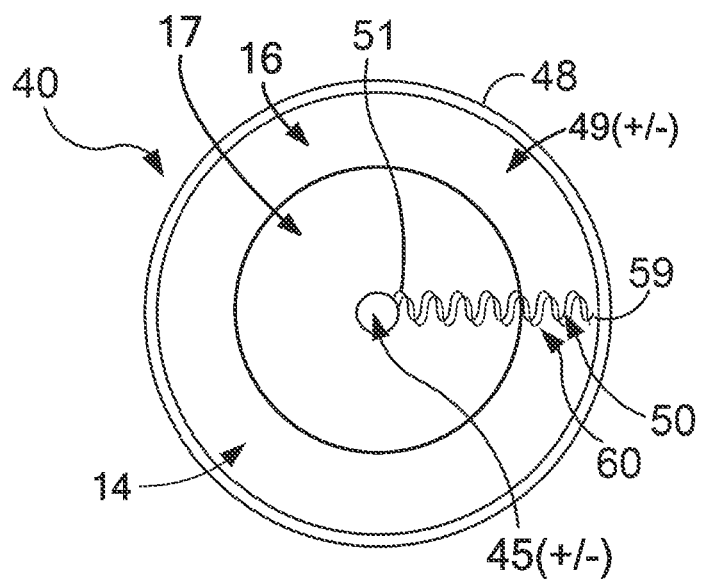
FIG. 25 is a schematic top view of the test disc of FIG. 24 with an exemplary target ssNA molecule hybridized with the probe ss/pssNA molecule to form a hybridized complex, which bridges the gap between the two electrodes in an embodiment of the present invention.

FIGS. 1B, 25 show a target ssNA molecule 60 and probe ssNA molecule 50 with complementary base pairs, which thus form a double-stranded hybrid duplex. If the tail 59 comprises adjunct molecules, the target ssNA molecule 60 may only hybridize with the proximal portion of the template ssNA molecule 50, leaving a portion of the tail un-hybridized. Or, as shown in FIG. 5D, depending on the extent to which complementary base pairing takes place between the two nucleic acid strands, the target ssNA molecule 60 may only partially hybridize with the probe ssNA molecule 50. The electrical characteristics of the double-stranded hybrid, partially double-stranded hybrid, or non-paired probe nucleic acid molecules 50 are analyzed and used in detecting the presence of the specific nucleic acid sequence of interest within the biological fluid 17.

Figure 2:
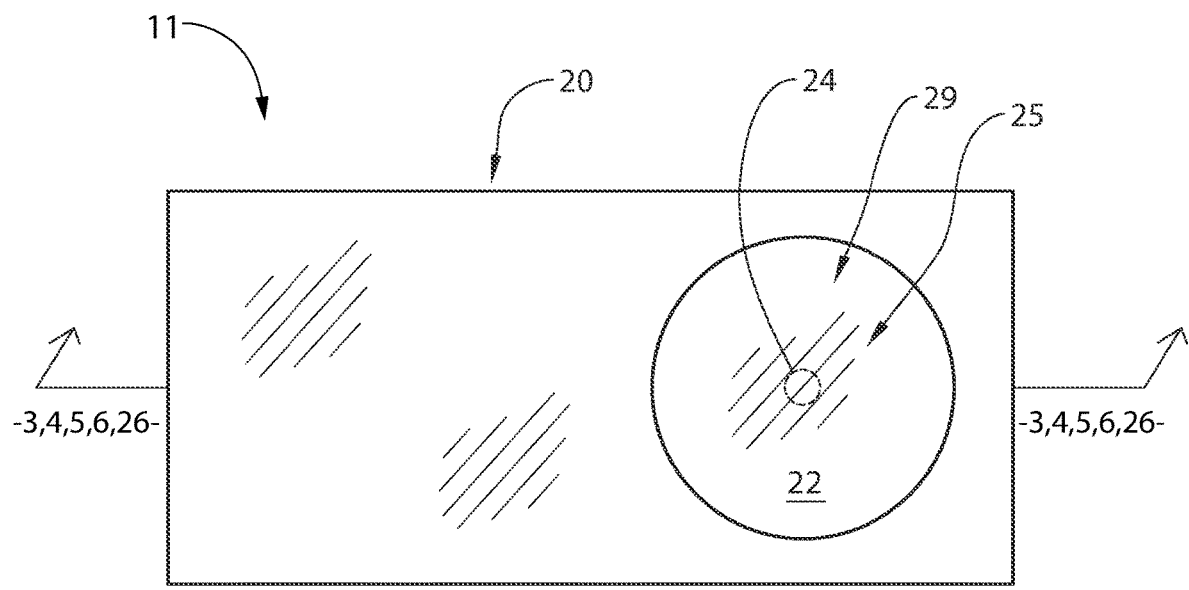
FIG. 2 is a top view schematic of a cartridge of an embodiment of the present invention with a cylindrical well which both functions as a specimen-receiving aperture for receiving a sample biological fluid and also serves as a disc-receiving aperture for receiving a test disc.
Figure 3:
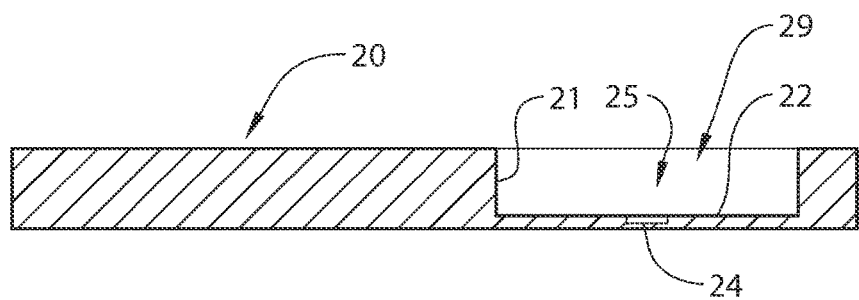
FIG. 3 is a cut view schematic of the cartridge of FIG. 2 (taken from line—3, 4, 5, 6, 26—of FIG. 2) in an embodiment of the present invention.

FIGS. 2-3 show the cartridge 20 (which is preferably disposable) having a top surface configured with a concave well 25 with walls and floor defining the open-top space of the specimen-receiving aperture, which has a depth and width sufficient to accommodate the volume of biological fluid 17 that is required for testing. In the aspect shown in FIGS. 4A-4C, 5A-5D, 6A-6E, 9, 26A-26D, the concave well 25 also serves as a disc-receiving aperture for receiving the disc 40. When the disc 40 is installed into the well 25, the disc outer cylindrical wall is adjacent to the well inner wall 21. So, the size and shape of the concave well 25 corresponds to the size and shape of the disc 40. In contrast to this aspect of the invention, in another aspect (FIGS. 10-13), the concave well 25 functions as a specimen-receiving aperture, but the disc-receiving aperture is a separate structure within the cartridge 20.

In an aspect of the invention shown in FIGS. 4A-4C, 5A-5D, the bottom 22 of the concave well 25 is preferably configured with an electrically conductive element 24, which, when the disc 40 is installed in the concave well 25, provides electrical power to the central first conductor 45 of the disc 40. The power to the electrically conductive element 24 is supplied by an external power source.

Figure 4A:
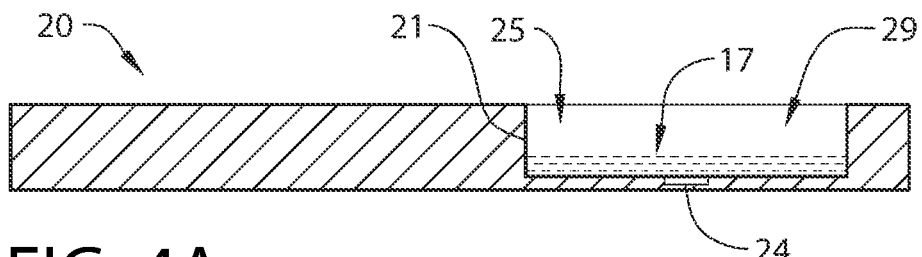
FIG. 4A is a cut view schematic of the cartridge of FIG. 2 (taken from line —3, 4, 5, 6, 26—of FIG. 2) configured with a concave well, with a sample biological fluid (which lacks the target virus carrying target RNA) introduced into the concave well in an embodiment of the present invention. a biological sample fluid.
Figure 4B:
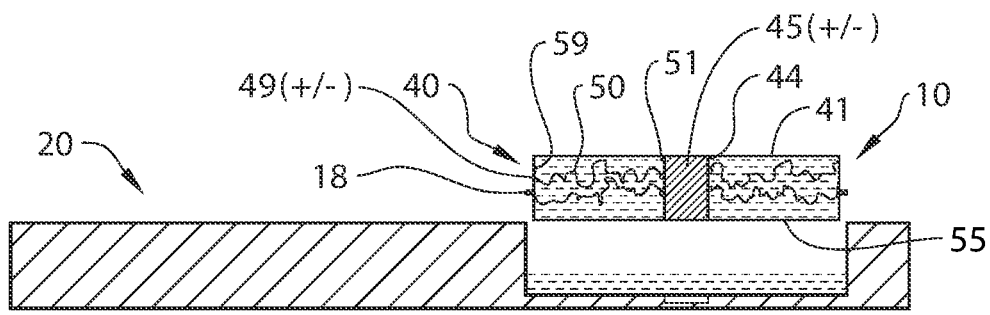
FIG. 4B is a cut view schematic of the cartridge of FIG. 2 (taken from line—3, 4, 5, 6, 26—of FIG. 2) with the biological sample fluid introduced into the concave well and with a test disc (enclosing the probe) in position to be moved into the concave well.
Figure 4C:
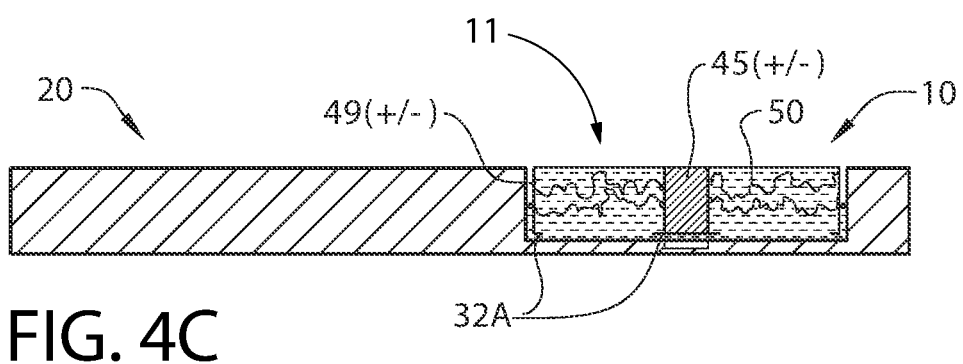
FIG. 4C is a cut view schematic of the cartridge of FIG. 2 (taken from line—3, 4, 5, 6, 26—of FIG. 2) with the bottom of the test disc open to allow mixing of the reagent with the biological sample fluid, but no target viral RNA is present, so no target RNA is unwound or is annealed to the ss/pssNA probe.

Schematics of performing the inventive rapid test are shown in FIGS. 4A-4C and FIGS. 5A-5D and FIGS. 6A-6E. Each of these sets of figures are schematics of cut views of the cartridge 20 with a test disc 40 (carrying probe 50) to be inserted within the cartridge well 25. The first set of figures, FIGS. 4A-4C, show testing of a biological sample fluid 17 that lacks the target virus. The second set, FIGS. 5A-5D, show the same test, but with the target virus 15 contained within the sample biological fluid 17; in this set, partially hybridized complexes are formed. The third set of figures, FIGS. 6A-6E, show the same test, and again the target virus 15 is contained within the sample biological fluid 17, but in this set, the hybridization is complete. These sets of figures also illustrate that the cylindrical wall of the test disc 60 may serve directly as the second electrode, as opposed to the aspect shown in FIG. 1A in which a wall-like cylindrical metallic border is disposed inwardly of, and adjacent to, the outer wall of the disc's outer housing.

To perform the rapid test, the technician obtains a test disc 40 and a corresponding test cartridge 20, with the test disc 40 carrying within it probe ss/pssNA molecules 50 that comprise at least a template strand 53 complementary to the specific nucleic acid sequence of interest, the target ssNA molecule 60. The biological fluid 17 is obtained, such as by collecting saliva expectorated by a person who is being tested for the presence of the specific virus of interest.

As seen in FIG. 4A, the sample/specimen fluid 17 is introduced into concave well 25. In an aspect of the invention, the fluid 17 is introduced in its native state. In another aspect of the invention, the fluid 17 is chemically or mechanically pre-treated before being deposited into the concave well 25. In an additional aspect, the fluid 17 is deposited into the concave well 25 and a reagent is added to the concave well 25 to mix with the fluid 17. The reagent serves to open the viral protein capsid or viral protein capsid and envelope and to unwind the viral nucleic acid. When the target nucleic acid sequence comes from an RNA virus, the reagent may, for example, include one or more RNA helicases to unwind the RNA. Similarly, if the target is a DNA virus, a DNA-specific helicase may be included in the reagent for unwinding the DNA.

The test disc 40 is then inserted into the cartridge well 25, as seen in FIG. 4B.

Structural features, such as gasket 18, may be included to contain the sample fluid 17 to prevent spillage during insertion of the disc 40.

As seen in FIG. 4C, the test disc 40 is opened to allow the fluid 17 to mix with the contents of the test disc 40, which at least includes the probe nucleic acid molecules 50. In an example, the bottom wall 55 of the test disc 40 may be fully or partially removed (such as by rotation as in FIG. 7 or by sliding to the side). In an aspect of the invention, the reagent is not added to the concave well 25 before insertion of the test disc 40 (as described above) but is instead carried within the disc 40. In another aspect of the invention, a portion of the reagent is added to the well 25 before insertion of the test disc 40 and another portion of the reagent is carried within the disc. The reagent may be in fluid form or may be in particulate form, such as freeze-dried reagent.

The fluid 17 is mixed with the reagent with the resulting sample-reagent solution washed over the probe nucleic acid molecules 50 within the test disc 40. An electrical current is applied to the disc 40, such as by or through the cartridge 20.

In the example of FIGS. 4A-4C, no hybridization occurs because the sample fluid 17 does not contain the virus with the target viral RNA. Thus, when the electrical sensing device 70 reads the electrical parameter (such as conductivity or resistance) within the circuit, there is no change from the reference value of the electrical parameter, because the probe nucleic acid molecules 50 remain in their original non-hybridized state. The detection circuit is in a first state (a non-detection state) when the target ssNA is absent, which corresponds to the non-detection state readings taken for comparison before introduction of the bodily fluid or when taken for comparison when saline solution is introduce into the test disc for a baseline reading. A predetermined array of conductivity values is preferably prepared before usage of the electrical sensing device 70.

Figure 5A:
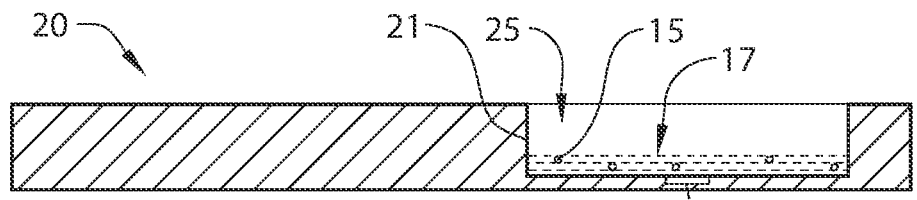
FIG. 5A is a cut view schematic of the cartridge of FIG. 2 (taken from line—3, 4, 5, 6, 26—of FIG. 2) configured with a concave well, with a sample biological fluid including the target virus introduced into the concave well in an embodiment of the present invention.
Figure 5B:
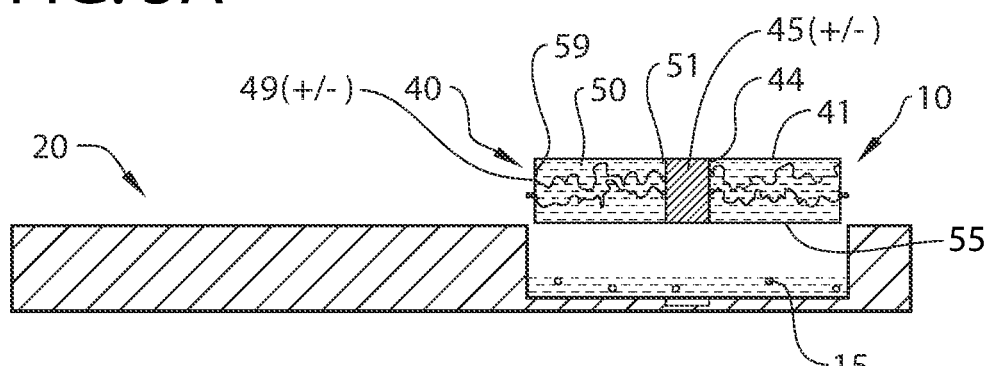
FIG. 5B is a cut view schematic of the cartridge of FIG. 5A with a test disc (enclosing the probe) in position to be moved into the concave well in an embodiment of the present invention.
Figure 5C:
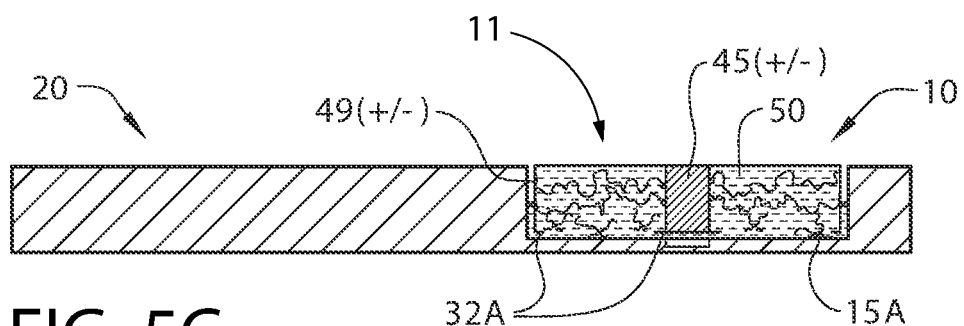
FIG. 5C is a cut view schematic of the cartridge of FIG. 5B with the bottom of the test disc open to allow mixing of the reagent with the biological sample fluid, which opens the virus and unwinds the target viral RNA.
Figure 5D:
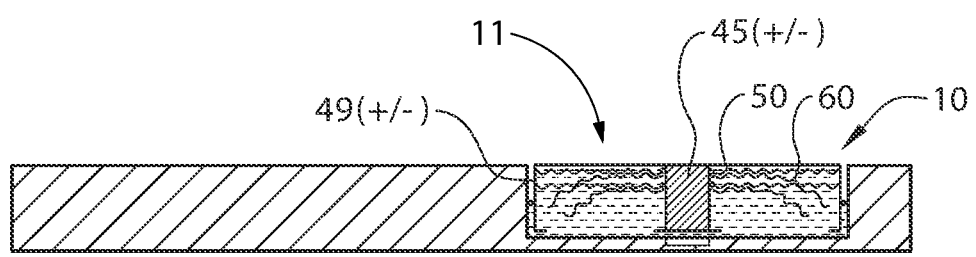
FIG. 5D is a cut view schematic of the cartridge of FIG. 5C with the bottom of the test disc open showing the target viral RNA partially hybridized with the probe.

FIGS. 5A-5D show the same testing method, but in this case, the biological fluid 17 contains the virus 15 with target RNA. Thus, when the reagent is mixed with the fluid 17, the virus is denatured and the nucleic acid is unwound, as seen in FIG. 5C. In FIG. 5D, fragments of the viral nucleic acid have partially hybridized with the probe nucleic acid molecule 50. Electrical current is applied to the disc 40, and electrical parameters are then read by the electrical sensing device 70. The detection circuit is in a second state, a partial hybridization state, when the target ssNA molecules are partially hybridized with the probe nucleic acid molecules 50. For example, the partially hybridized complex may have a conductivity value higher than the non-detection reference value. The electrical parameter value obtained is compared to values in a predetermined array of conductivity values to determine the presence and concentration of target ssRNA, or other related ssRNA sequences. The partially hybridized state may be associated with multiple sub-states and values reflecting the degree of hybridization.

Figure 6A:
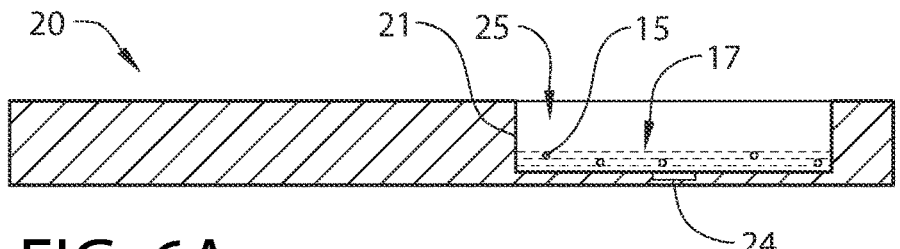
FIG. 6A is a cut view schematic of the cartridge of FIG. 2 (taken from line—3, 4, 5, 6, 26—of FIG. 2) configured with a concave well, with a biological sample fluid including a virus carrying the target RNA introduced into the concave well in an embodiment of the present invention.
Figure 6B:
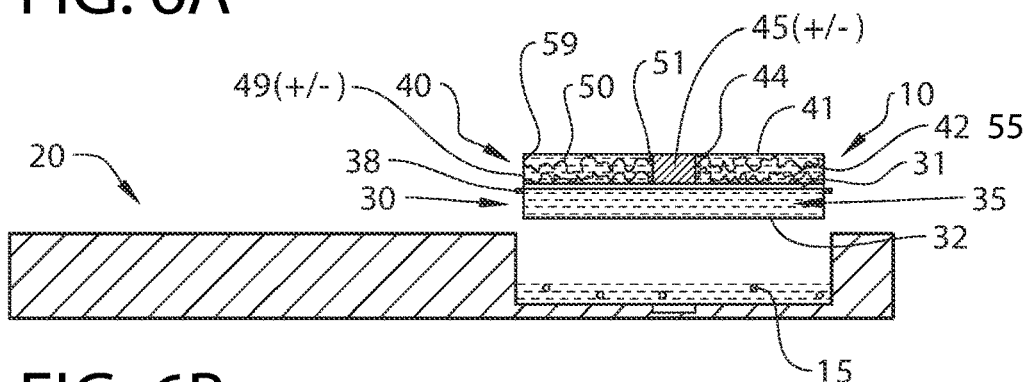
FIG. 6B is a cut view schematic of the cartridge of FIG. 6A with the biological sample fluid including the virus of interest introduced into the concave well and with a test disc (with an interior compartment enclosing probe molecules and with a separate reagent compartment) in position to be moved into the concave well.
Figure 6C:
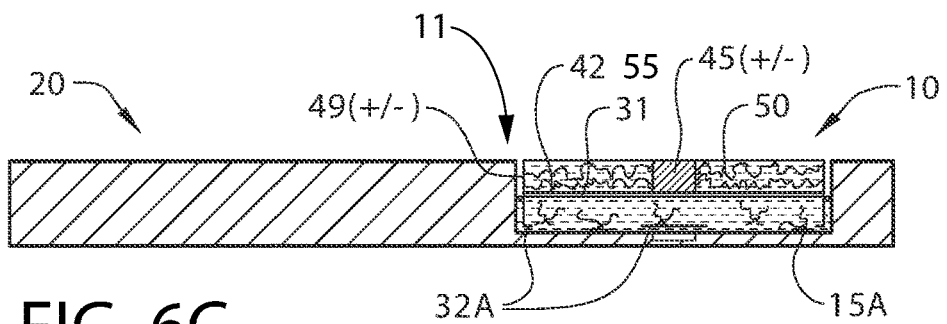
FIG. 6C is a cut view schematic of the cartridge of FIG. 6B with the bottom of the reagent compartment open to allow mixing of the reagent with the biological sample fluid, which opens the virus and unwinds the target viral RNA.
Figure 6D:
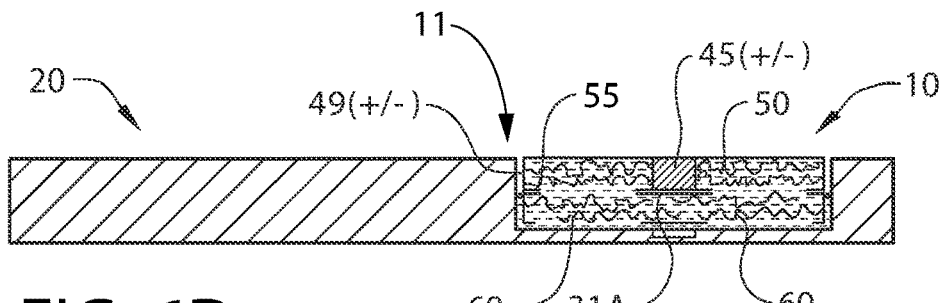
FIG. 6D is a cut view schematic of the cartridge of FIG. 6C with the bottom of the probe compartment of the disc open to allow the unwound RNA to enter the bottom of the probe compartment.
Figure 6E:
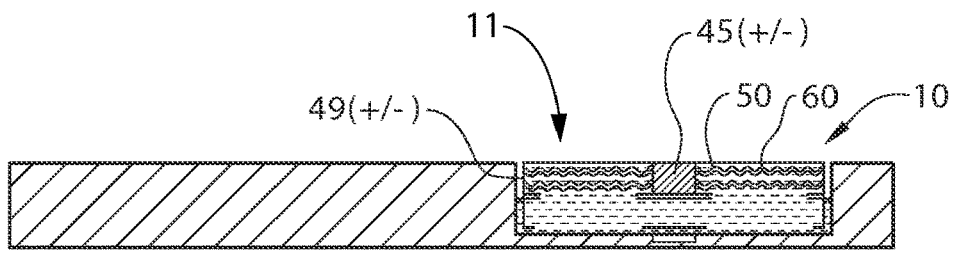
FIG. 6E is a cut view schematic of the cartridge of FIG. 6D showing the unwound single-stranded viral RNA molecules fully hybridized with the probe molecules in an embodiment of the present invention.

FIGS. 6A-6E illustrate full hybridization occurring by the end of the test. Also, FIGS. 6A-6F disclose an aspect of the invention in which the test disc 40 additionally comprises a reagent compartment 30 separate from the compartment of the disc carrying the electrodes. The reagent compartment 30 is designed to contain the reagent, but to be openable to release the reagent into the electrode-containing portion of the disc 40. In one exemplary design, the reagent compartment 30 comprises an interior compartment within the disc 40. In another exemplary design, the reagent compartment 30 comprises a disc-shaped distinct portion attached to the conductor-containing disc-shaped portion, as shown in FIGS. 6B-6E. The disc-shaped separate reagent compartment comprises compartment side walls, a compartment ceiling 31, and a compartment floor 32. The reagent compartment side walls are preferably cylindrical and generally aligned with the walls of the electrode-containing compartment. As seen in FIGS. 6C, 6D, both the compartment ceiling and the compartment floor (which in these figures is also equivalent to disc floor 55) are openable.

Figure 7:
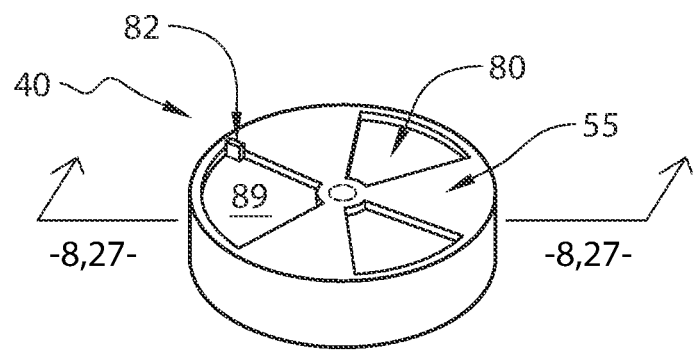
FIG. 7 is a schematic perspective view of the bottom of a test disc illustrating an exemplary mechanical/structural opening mechanism in an embodiment of the present invention.
Figure 8:
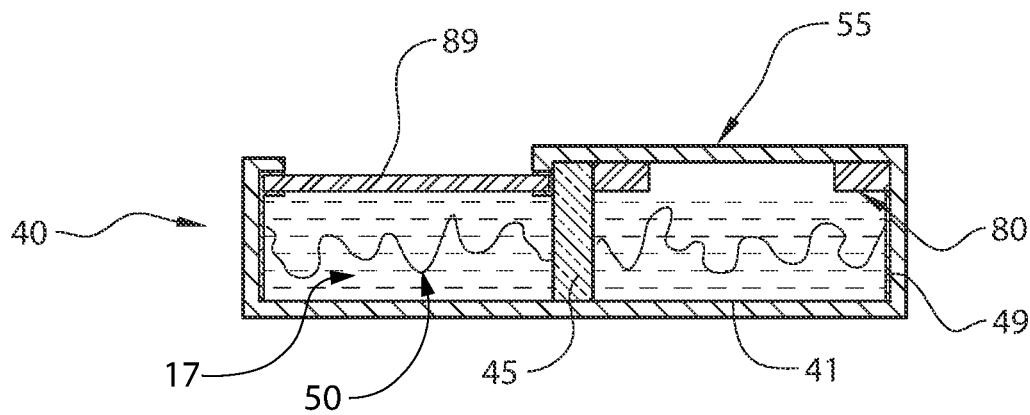
FIG. 8 is a cut view schematic taken along lines—8, 27—of FIG. 7 of the test disc with the two-part mechanical/structural opening feature.

When a reagent compartment 30 is included, in one aspect, the reagent is allowed to mix with the sample biological fluid 17 before the resulting sample-reagent solution is introduced to the probe nucleic acid molecules 50. The two-compartment disc 40 may be designed in various ways to allow opening of the reagent compartment 30. In one example, the lower reagent compartment 30 is opened, such as by removing or opening the bottom floor 32, to allow the reagent to contact the virus within the sample fluid 17. (An exemplary mechanism, projection 82, to open the bottom floor of disc 40 is shown in FIGS. 7-8.) Then, in a separate step, the bottom floor of the upper probe compartment and/or the reagent compartment ceiling 31 are opened to allow the sample-reagent solution to contact the probe nucleic acid molecule 50. FIG. 6D shows the reagent compartment open to the probe compartment.

The example of FIGS. 6A-6E shows similarities to the steps of FIGS. 4A-4C, 5A-5D, but with the difference that the final step results in a fully hybridized state. In this example, the biological fluid 17 contains the target virus 15, and the target ssNA molecule 60 fully hybridizes with the probe nucleic acid molecule 50. When electrical current is applied to the disc 40 and the electrical parameters are read by the electrical sensing device 70, the fully hybridized complex will have different electrical parameters then the two earlier examples. For example, the conductivity value may be higher than the reference value and higher than the partially hybridized conductivity value, and the resistance may be lower. The electrical parameter result is compared to values in the predetermined array of conductivity values to determine the presence and concentration of target ssRNA. The detection circuit is in a third state, fully hybridized state, when the target ssNA molecules are fully hybridized with the probe nucleic acid molecules 50.

These examples of three conductivity values are provided for understanding of the invention, but the predetermined array of conductivity values preferably includes many more conductivity values determined in advance of the testing and stored in the electrical sensing device 70 for comparison with the test results and output to the user via the signaling device 75.

Figure 9:
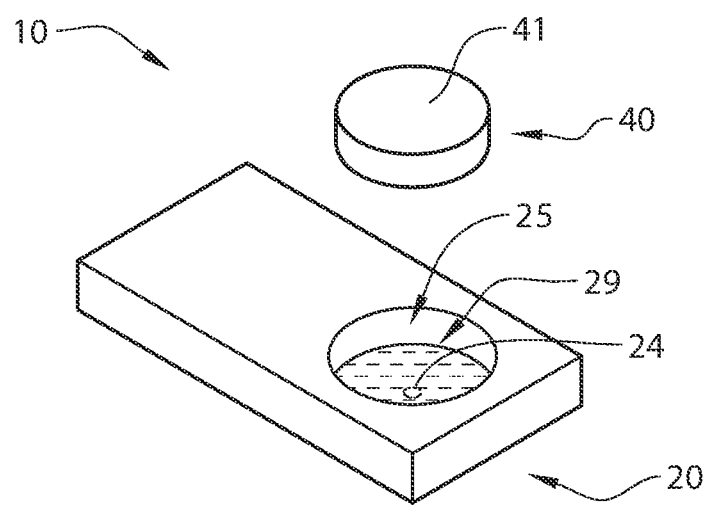
FIG. 9 is a top perspective view of a cartridge with the test disc of FIG. 7 inverted to cause the two-part mechanical/structural opening feature to face downward into the well (serving as both a specimen-receiving aperture and a disc-receiving aperture) and with the test disc aligned with, and ready for insertion into, the well, which is disposed on the top of the cartridge.

FIGS. 7-9 illustrate an aspect of the invention in which the bottom side 55 of the disc 40 (FIG. 7 is shown with the disc 40 inverted, so the disc bottom 55 is oriented to the top) has an exemplary structural opening mechanism, whereby the disc 40, after insertion into concave well 25, can be opened to allow the contents of the disc 40 to be mixed with the sample fluid 17. This is shown as a cooperative structural opening mechanism disposed on the disc bottom 55, which, when inserted into the well 25, is adjacent to the bottom 22 (FIG. 2) of the well 25. The structural opening mechanism includes an outer planar partial disc bottom 55 and an inner planar rotatable element 80. The top surface 89 of the inner planar rotatable element 80 is adjacent to the bottom surface of the outer planar partial disc bottom 55. In the open position, the openings in the outer planar partial disc bottom 55 are aligned with the openings in the inner planar rotatable element 80. In the closed position, the openings in the outer planar partial disc bottom 55 are inverse or opposite to the openings in the inner planar rotatable element 80. Thus, when in the closed position shown in FIGS. 7-8, 27, the disc 40 is sealed.

When the disc 40 that includes the structural opening mechanism is introduced into the concave well 25, the rotatable element 80 is rotated to align the openings of the outer planar partial disc bottom 55 with the openings of the inner planar rotatable element 80. In an aspect, a projection 82 (FIG. 7) protrudes from the top surface 89 of the rotatable element 80. It is engaged against the well bottom 22 to enable manual rotation of the rotatable element 80 when access is only available from the top surface 41 of the disc 40.

Another embodiment of the invention is shown schematically in FIGS. 10-13. In this embodiment the concave well 25 does not serve as a disc-receiving aperture. Instead, the disc-receiving aperture is disposed within a portion of the cartridge 20 with that portion being lower than the well 25. This allows the disc 40, when fully inserted into the aperture, to be positioned below the well 25. The advantage of this embodiment is that the fluid 17 can be gently moved by gravity onto the probe nucleic acid molecule 50 disposed below it, which may cause less turbulence than the open bottom disc 40 described above.

Figure 10:
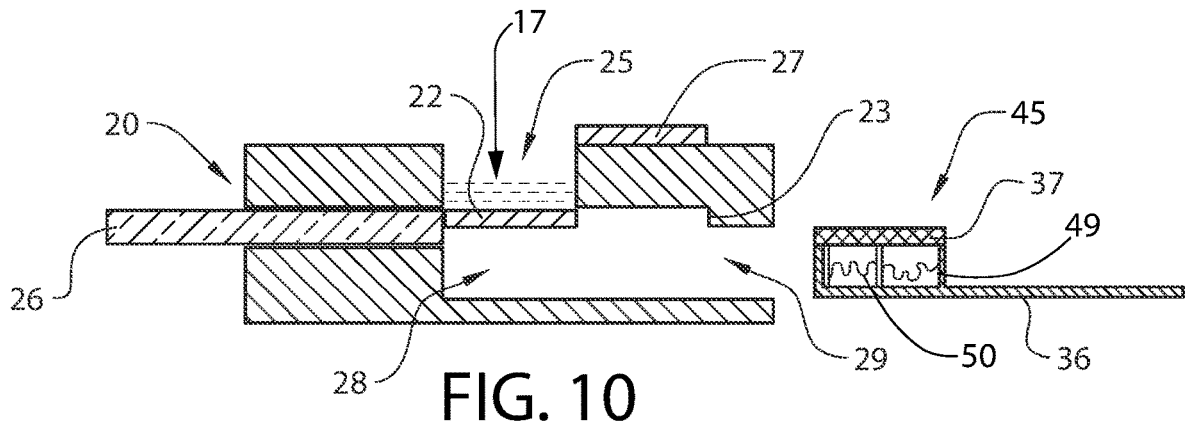
FIG. 10 is a schematic of a cut view taken through the middle of a cartridge (not illustrated in perspective, but having a top view as in the cartridge of FIG. 2, and having a depth of at least twice the cartridge of FIG. 3) of an embodiment of the present invention, showing the introduction of the biological fluid into the upper well (specimen-receiving aperture) and showing the alignment of the test disc for insertion into a disc-receiving aperture disposed on the side of the cartridge.

FIG. 10 shows the test disc 40 aligned with, and ready for insertion into, the cartridge's side disc-receiving aperture. The disc-receiving aperture is defined by an aperture roof, aperture side walls, an aperture back wall, an aperture floor, and an aperture side opening. The aperture side opening has a proximal opening area and extends inwardly to below the concave well 25 with aperture back wall generally aligned with a corresponding well side wall. A disc-insertion tab 36 is a projection that extends from the disc 40 a sufficient distance outwardly to allow manual insertion of the disc 40 into the disc-receiving aperture, as shown.

Figure 11:
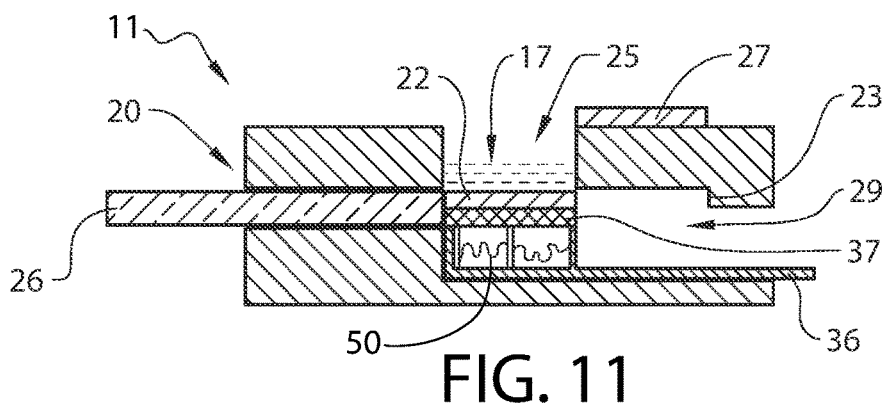
FIG. 11 is a schematic of a cut view of the cartridge of FIG. 10 showing the test disc inserted into the disc-receiving aperture of the cartridge.
Figure 12:
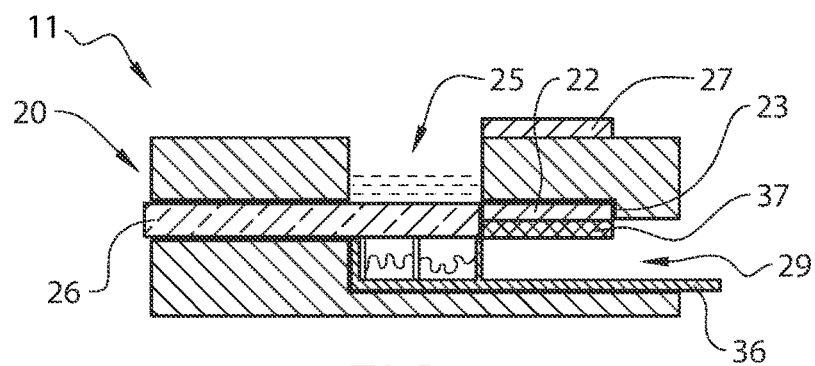
FIG. 12 is a schematic of a cut view of the cartridge of FIG. 11 showing the top lid of test disc and the bottom wall of the concave well removed by the extending of the seal-removal pusher.

As seen in FIG. 11, the disc-insertion tab 36 has been used to manually push the disc 40 to the end of the disc-receiving aperture, which positions the disc 40 directly below the concave well 25 containing the fluid 17. The disc 40 remains in this position while a seal-removal pusher 26 is used to remove the top lid 37 of test disc 40 and the openable bottom wall 22 of the well 25, as seen in FIG. 12.

Figure 13:
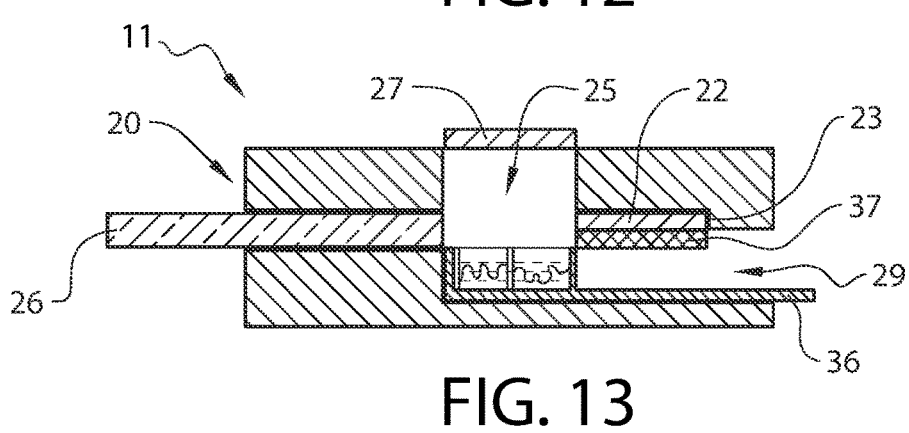
FIG. 13 is a schematic of a cut view of the cartridge of FIG. 12 showing a disc top lid of test disc and the bottom wall of the concave well have been removed, with the seal-removal pusher retracted, and with a cartridge well cap slid in place to form a closure for the testing space.

The sample fluid disc-receiving aperture 2917 potentially containing the target virus moves by the force of gravity onto the probe nucleic acid molecule 50 below it, which is now exposed within the disc 40, as seen in FIG. 13. In an aspect, a cap 27 may be manually placed onto or across the opening at the top of the walls of the wall 25. This may be desirable if the cartridge is to be inverted or agitated to increase mixing of the reagent-fluid solution with the probe nucleic acid molecules 50. If agitation is desired, the agitation may include manual shaking, centrifuging, mechanical shaking by the electrical sensing device 70 or a separate machine, or the like.

Figure 14:
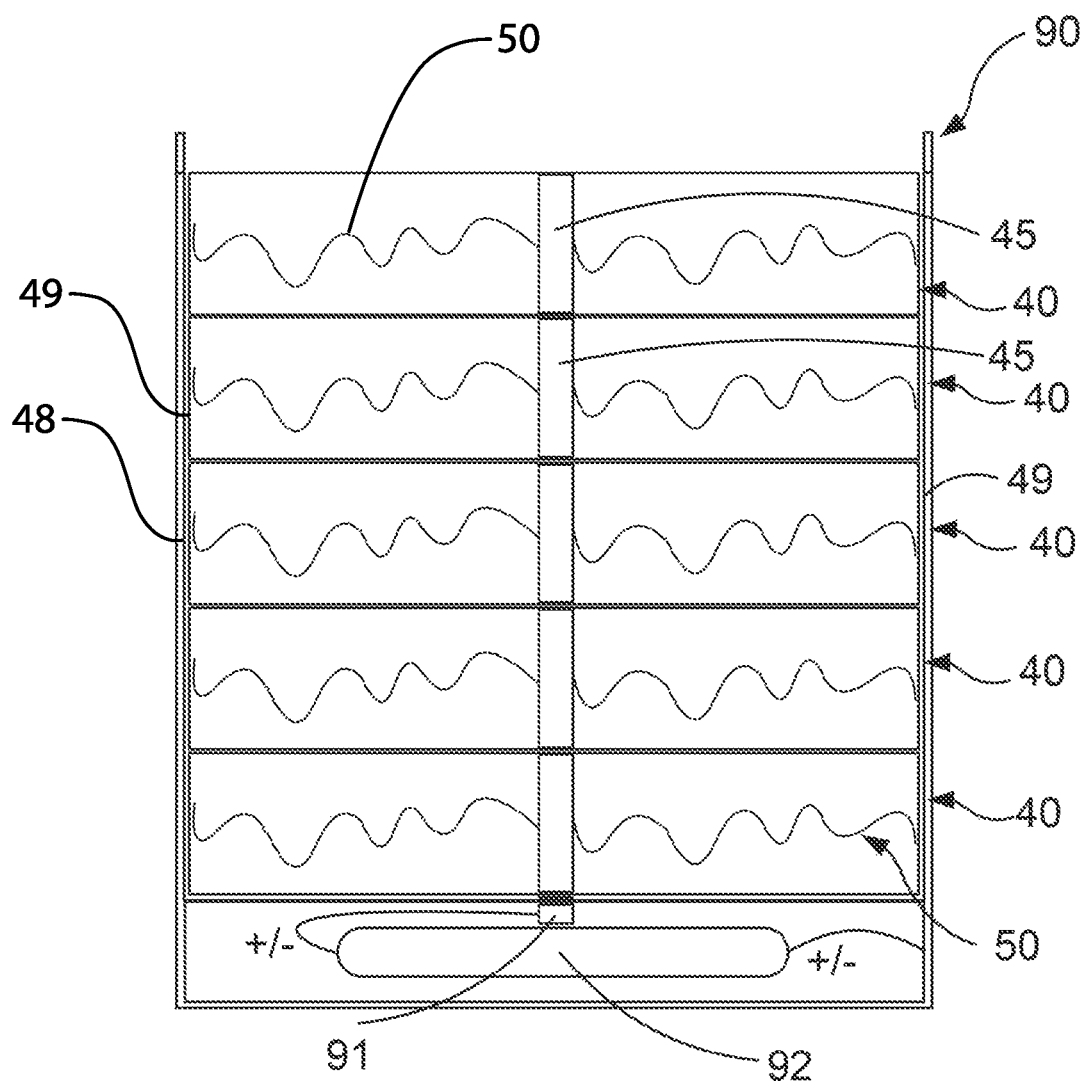
FIG. 14 is a cut view schematic of a pre-operation multi-disc container powered to maintain, before use of the test disc, the ss/pssNA probes held in an orientation bridging the space between the first central conductors and the second outer conductors of multiple discs, which serves to keep the test discs in readiness for use.

In an additional aspect of the invention as seen in the schematic of FIG. 14, the test system further comprises a multi-disc container 90 that is sized and configured to hold multiple discs 40 before they are to be utilized for testing. The multi-disc container 90 includes a power source 92 to provide current via multi-disc container electrode(s) 91 to the contained discs 40. In this aspect, the power provided to the contained discs 40 assists in maintaining each probe nucleic acid molecule 50 in readiness for use in the stretched orientation wherein it bridges the gap between the inner first conductor 45 and the outer second conductor 49. Thus, the probe nucleic acid molecule 50 in the contained discs 40 is held in the functional, expanded position in anticipation of usage, which may potentially decrease the time needed for the test to be performed and may result in more accurate test results.

FIGS. 15-17 are schematics illustrating the attachment of probe nucleic acid molecules 50 to the first conductor 45. FIG. 15 shows an aspect of the invention in which random attachment occurs when the head 51 of the template 50 is anchored to the first conductor 45.

Figure 21:
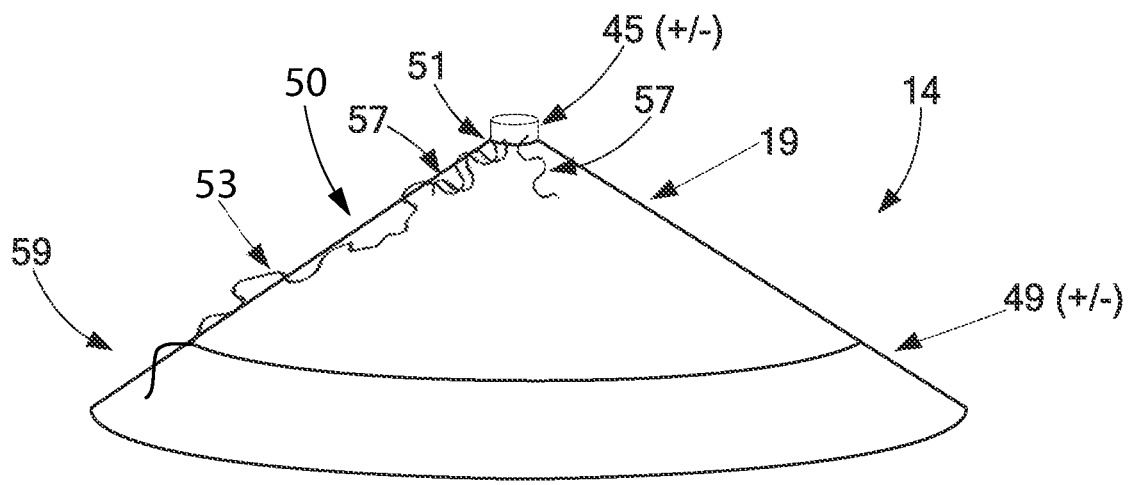
FIG. 21 is a schematic front view of a truncated cone construction of the second embodiment of the test disc of the invention, which illustrates the attachment of the head of the probe molecule to the first electrode via a short strand of complementary anchor ssNA and the attachment or attraction of the tail of the probe molecule to the second electrode.

In another aspect of the invention, the heads 51 of the probe nucleic acid molecules 50 are anchored onto the rod 45 in aligned rows. The aligned rows 50A, 50B, 50C, 50D are illustrated in FIG. 16. The head 51 may be immobilized onto the conductor 45 by a head sequence (X), a covalent bond, or an anchor oligonucleotide sequence may be attached to the rod 45 with the head 51 then attached to the anchor oligonucleotide sequence, where the anchor oligonucleotide sequence may be, for example, a protein or polymerase. The proximal end of the probe nucleic acid molecule 50 contains a nucleic acid sequence complementary to the anchor oligonucleotide sequence. In this aspect the probe nucleic acid molecule 50 is partially double stranded due to the duplex formed with the anchor oligonucleotide sequence, as seen in FIG. 21.

The schematics of FIGS. 16-17 show methods to align the rows 50A, 50B, 50C, 50D of probe nucleic acid molecules. FIG. 16 shows rods or strips 81 blocking portions of the rod 45 and, thus, preventing attachment of the probe nucleic acid molecules 50 in the blocked areas. FIG. 17 shows an end view of the rod 45, showing a single mechanism of a row of mechanisms 83 (aligned behind the mechanism shown, so not seen) that allow a strip of the rod 45 to be exposed for attachment of multiple probe nucleic acid molecules 50 in a row. A first row is attached, and then the rod 45 is rotated to allow another row to be deposited. This provides control of the spacing of the probe nucleic acid molecules 50. In another aspect, the conductor 45 may be chemically treated and then chemically etched to prescribe multiple lines that permit attachment of the probe nucleic acid molecules 50 in rows.

Figure 18:
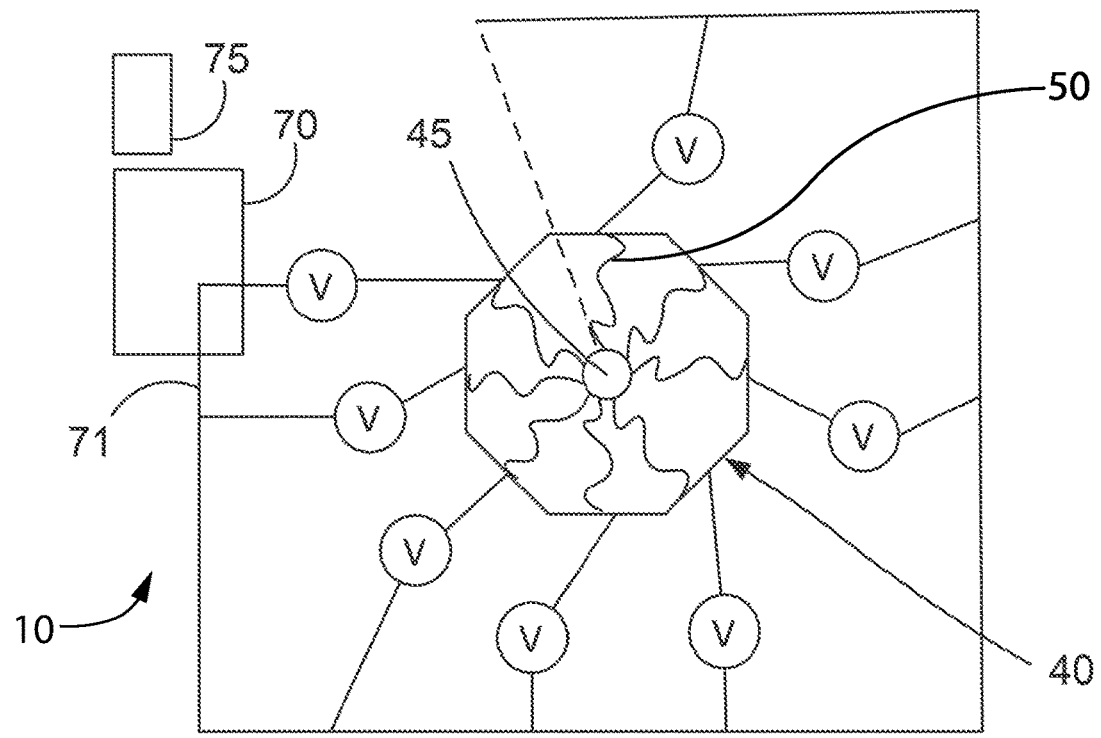
FIG. 18 is a schematic view of an aspect of the invention in which an electrical sensing subsystem of a test system of the present invention provides multiple readings with a reading from each of the aligned rows of probe nucleic acid molecules.

FIG. 18 is a schematic view of an aspect of the invention in which the test system 10 of the present invention provides multiple readings with a reading from each of aligned rows of probes 50 or from each of groups of rows of probes 50. For clarity of discussion, FIG. 18 shows an octagonal test disc 40 with eight wall segments or plates and eight circuits to be read by the electrical sensing device 70, but the system 10 of the invention may include less than or many more than eight wall segments and circuits. The wall segments/plates are electrically insulated from each other. In this aspect, the probes 50 are attached in aligned rows to the first conductor 45, as described in relation to FIGS. 16-17. The probes 50 stretch outwardly from the first conductor 45 to the wall segments, where they are also attached or attracted. (The wall segments may include only the disc outer wall serving as the second conductor, as shown, or may include both the disc outer wall and the inner wall-like cylindrical metallic border disposed inwardly of, and adjacent, to the outer wall of the disc's outer housing, as seen in FIG. IA).

In one aspect, a first row of probes 50 is attached to a first wall segment (functioning as conductor 49), and a second row of probes 50 is attached to a second segment, etc. In another aspect, multiple rows of probes 50 are attached to each wall segment. In either aspect, each wall segment is part of one circuit and is individually addressable, as in FIGS. 18-19, 29-30. The power and wiring for the circuit are preferably included within the cartridge and/or the electrical sensing device 70, and they are most preferably included in the electrical sensing device 70. One or more electrical parameters (voltage, voltage drop, resistance, or the like) of each circuit is read by the electrical sensing device 70.

Figure 19:
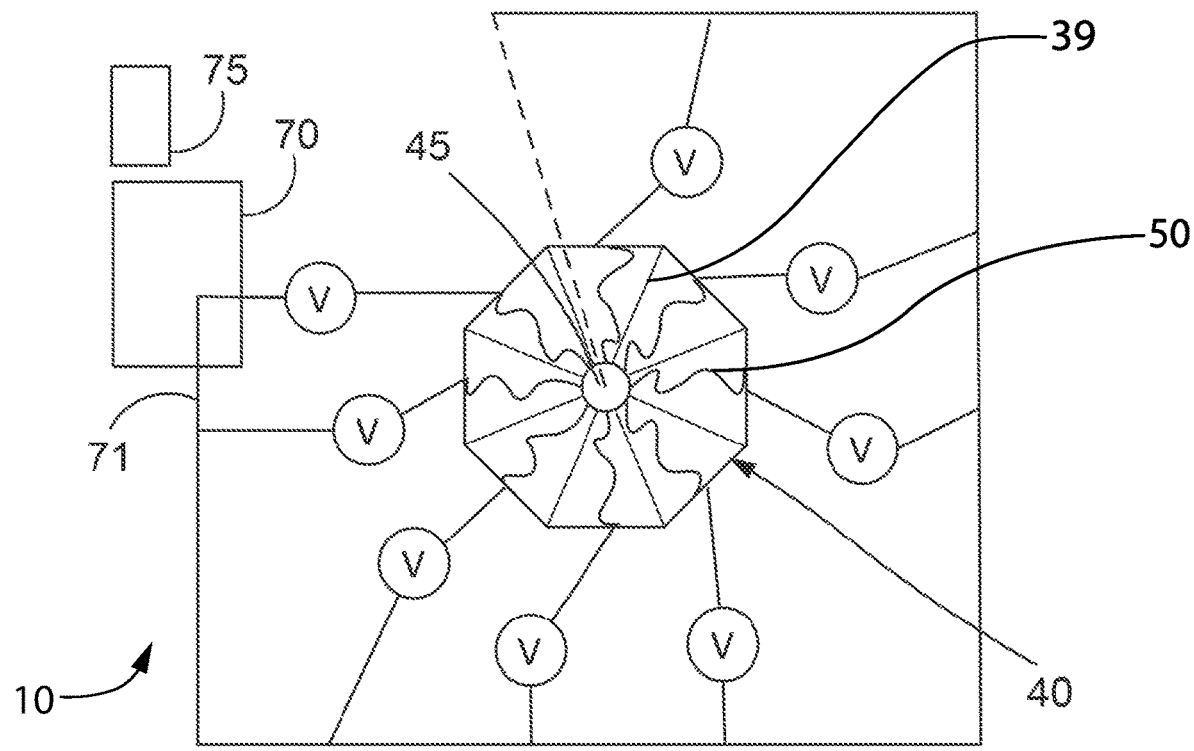
FIG. 19 is a schematic view of an aspect of the invention in which an electrical sensing subsystem of a test system of the present invention provides multiple readings with a reading from each of the aligned rows of probe nucleic acid molecules where the test disc also includes interior dividers.

FIG. 19 is a schematic view of a further aspect of the invention which functions similarly to the aspect of FIG. 18, but which additionally includes non-conductive (such as plastic) interior dividers 39 between the pie-shaped segments. The interior dividers 39 may facilitate deployment of the probes 50 into the disc but may be removed before introduction of the specimen fluid 17.

These multiple row aspects of the invention provides advantages in redundancy (performing multiple tests at one time) and in multi-target ssNA molecule detection, such as using one type of probe nucleic acid molecules in one row, a second type of probe nucleic acid molecules in second row, etc.

The schematics of FIGS. 20-27 illustrate a second embodiment of the test disc 40 in which a truncated cone construction 14 is disposed within the outer housing 48 of test disc 40. The truncated cone construction 14 comprises a wider lower cone portion with the narrow upper end of the cone truncated.

The probe ss/pssNA 50 bridge the gap between a center first conductor 45 at, or extending from, the truncated top area of the cone and a perimeter second conductor 49 at, and extending upwardly from, the lower perimeter at the base of the cone. The center first conductor 45 is electrically separated from the second conductor 49 by a non-conductive cone middle section 19, which may be plastic or other non-conductive material.

The conductive base second conductor 49 is disposed along the wider base (lower end in FIGS. 20-24) of the cone and extends upward from the base edge to below the middle of the cone. The base second conductor 49 may be disposed along the entire lower perimeter of the base or may be disposed only along one or more portions of the lower perimeter of the cone. The non-conductive section 19 functions to separate the first conductor 45 from the second conductor 49. As shown in the cut views of FIGS. 26B-26D and FIG. 27, the first conductor 45 may be supported by, and inset within, the non-conductive portion 19. The first conductor may comprise a nanowire, microwire, wire, nanorod, microrod, or other wire-like structure. The truncated cone construction 14 may be held in position adhesively or mechanically (such as by the tension provided by a spring 13). Or the cone construction 14 may be held by frictional engagement of the outer perimeter of the truncated cone construction 14 with the inner walls of the well 25.

The width and slant of the second electrode 49 function to allow the tail 59 to drag along the wide, slanted surface of the second conductor 49 with forces (such as electrical or electrostatic) attracting the tail 59 to the second conductor 49. When detecting the electrical parameters in the test using this disc 40 with a truncated cone construction 14, the resistance strength (or conductivity reading) can be an average over time to account for variations in resistance (or conductivity) caused by position changes of the tail along the second electrode 49 caused by, for example, Brownian motion.

As in the first structural embodiment of the test disc (FIGS. 1A-1B, 4B-4C, 5B-5D, 6B-6E, 8, 10-13), in this second embodiment, even though the probe nucleic acid molecules 50 bridge the gap between the first electrode 45 and the second electrode 49, they are preferably not attached tautly, but have a sufficient length of nucleic acid sequences to allow a lax or slack disposition. The additional length of the nucleic acid sequences allows for conformational change and constriction that occur when complementary binding of the probe 50 to the ssNA target 60 occurs. When hybridization occurs, the hybridized complex tends to be shorter than the probe ssNA 50, but the width of the slanted surface of the second conductor 49 functions to allow the shorter hybridized complex to remain electrically or electrostatically attracted.

Figure 20:
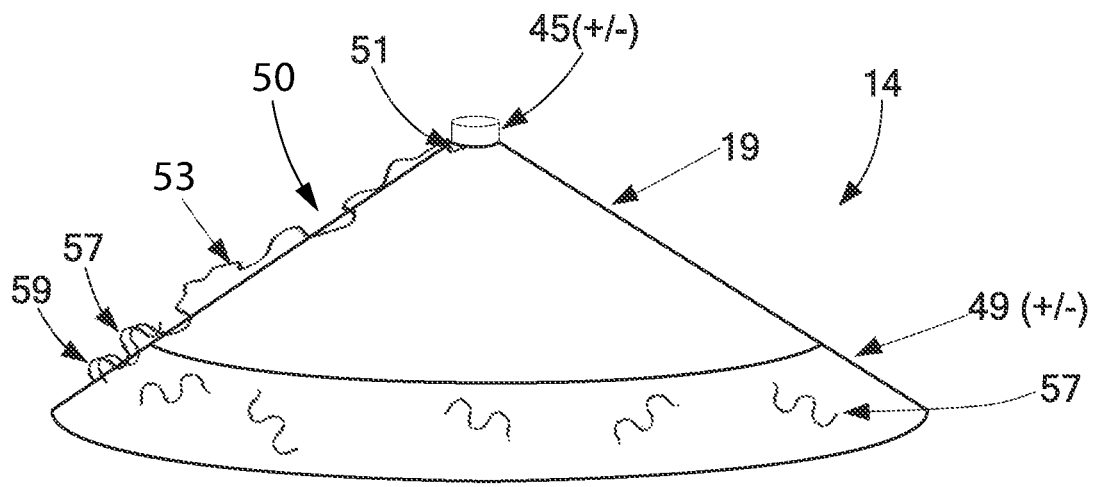
FIG. 20 is a schematic front view of a truncated cone construction of a second embodiment of the test disc of the invention, which illustrates the attachment of the head of a ss/pssNA probe molecule to a first electrode and the attachment or attraction of the tail of the probe molecule to the second electrode via a short strand of complementary anchor ssNA.
Figure 23:
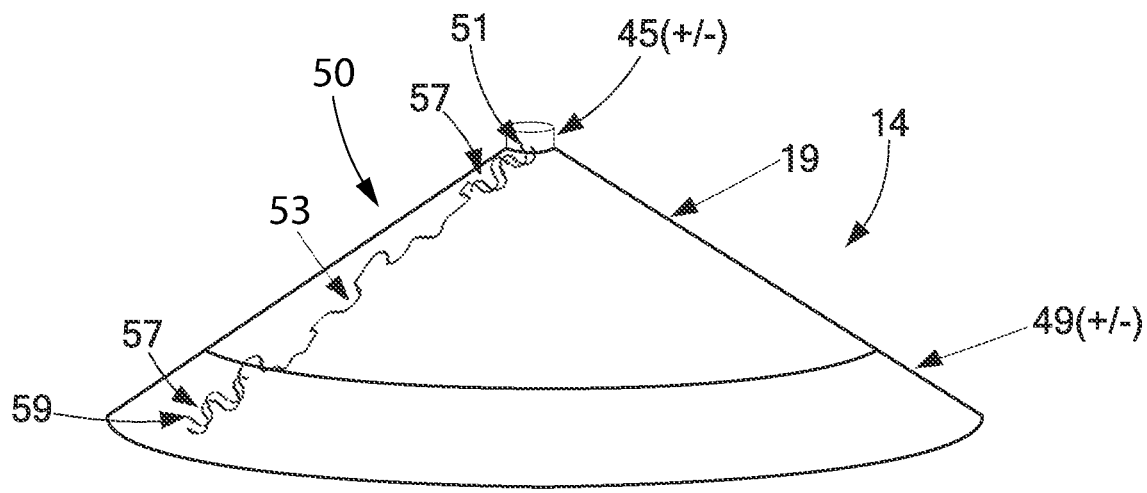
FIG. 23 is a schematic front view of a truncated cone construction of the second embodiment of the test disc of the invention, which illustrates the attachment of the head of the probe molecule to the first electrode via a short strand of complementary anchor ssNA and the attachment of the tail of the probe molecule to the second electrode via a short strand of complementary anchor ssNA.

FIGS. 20-21, 23 are schematic front views of the truncated cone construction 14 that illustrate aspects of the invention in which the head 51 and/or the tail 59 are attached to the first conductor 45 and/or second conductor 49 through the utilization of anchor strands of oligonucleotide sequences 57. One or two anchor strands 57 may be used as needed for attachment. An anchor strand 57 may be complementary to the head 51 or to the tail 59 of the probe 50, as seen in FIGS. 21 and 20, respectively. Or first and second anchor strands 57 that are complementary to the head 51 and to the tail 59, respectively, may be used, as seen in FIG. 23.

FIG. 20 illustrates a tail 59 of a probe nucleic acid molecule attached to the second electrode 49 via a short anchor strand 57. The anchor strand 57 includes bases that are complementary to the bases of the tail 59 of the probe nucleic acid molecule 50. Multiple ssNA anchor strands 57 are affixed to the second electrode 49, and then the probe nucleic acid molecules 50 are introduced. The tail 59 of a probe nucleic acid molecule 50 then hybridizes or anneals with one of the corresponding molecules of anchor ssNA 57, which attaches the tail 59 at the second electrode 49.

FIG. 21 shows the head 51 hybridized with anchor strands 57 for attachment to the first electrode 41 with the tail 59 attracted to the second electrode 49.

Figure 22:
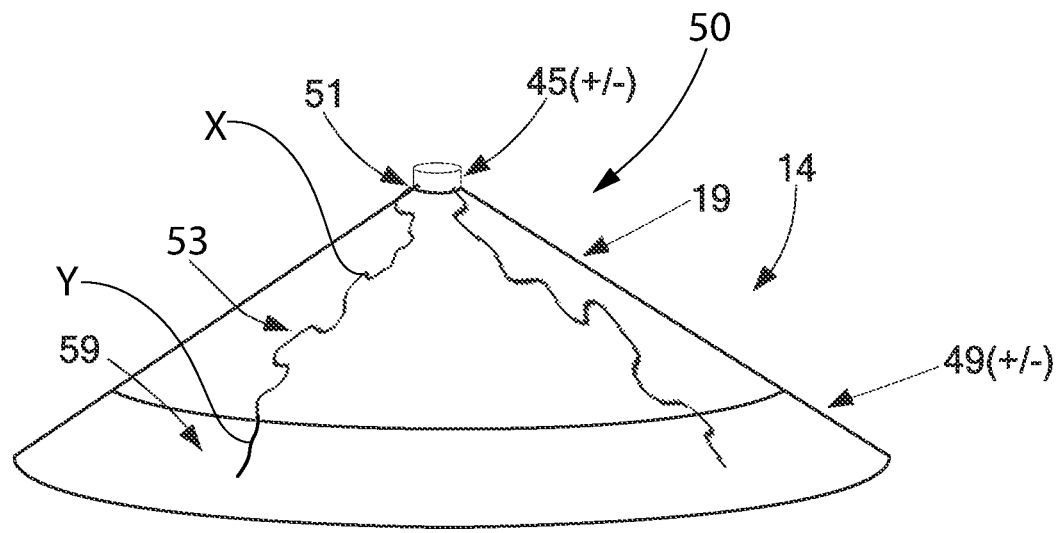
FIG. 22 is a schematic front view of a truncated cone construction of the second embodiment of the test disc of the invention, which illustrates the attachment or attraction of the probe molecule's head to the first electrode and of the probe molecule's tail to the second electrode and which illustrates a template portion, sequence (X), and sequence (Y) of the probe.

In FIG. 22, both the head 51 and tail 59 of the probe 50 are stabilized (attached to or attracted to) at the first electrode 45 by electrical or electrostatic attraction and without use of anchor ssNA 57. In this aspect, the template portion 53 of the probe 50 has a known sequence (X) attached to the head-facing portion of the template 53 and a known sequence (Y) attached to the tail-facing portion of the template 53.

In another aspect of the invention shown in FIG. 23, both the head 51 and the tail 59 of the probe nucleic acid molecule 50 are attached to or attracted to the corresponding electrode 45, 49 via short anchor strands 57. In this aspect, a first anchor oligonucleotide sequence 57 is attached to the first conductor 45, and a second anchor oligonucleotide sequence 57 is attached to the second conductor 49. The first anchor oligonucleotide sequence 57 is complementary to the head 51, and the second anchor oligonucleotide sequence 57 is complementary to the tail 59. The probe nucleic acid template sequence 53 that is complementary to the target nucleic acid sequence is disposed between the two anchor oligonucleotide sequences 57.

The top view schematic of FIG. 24 shows the test disc 40 with an outer housing 48 that encloses an interior chamber holding a truncated cone construction 14, which includes the electrically separated first conductor 45 and base second conductor 49.

As in the first embodiment, preferably the tail 59 is sufficiently long to trail along the slanted surface of the second electrode 49. This laxity is enabled by an extra length of nucleic acids disposed at the tail 59 beyond the length required to stretch between the conductors 45, 49, such as adjunct molecules.

Though the probe nucleic acid molecule 50 is shown in FIG. 24 as fully single-stranded, a portion of the probe nucleic acid molecule 50 may be double stranded. For example, the tail 59 may be double stranded while the remaining portion (the middle sequences to the sequences of the head 51) is single-stranded nucleic acid, as shown in FIG. 20. In another example shown in FIG. 23, when a ss/pssNA probe nucleic acid sequence has a head and tail attached to two anchor oligonucleotide sequences 57, both ends of the probe nucleic acid molecule 50 will be double stranded while the center, the template portion 53 of the strand, will be single stranded.

FIG. 25 shows a target ssNA molecule 60 and a probe ssNA molecule 50 with complementary base pairs, which together form a double-stranded hybrid duplex. Though this figure shows full hybridization. But, depending on the extent to which complementary base pairing takes place between the two nucleic acid strands, the target ssNA molecule 60 may only partially hybridize with the probe ssNA molecule 50 (as shown in FIG. 5D above). The electrical characteristics of the double-stranded hybrids, partially double-stranded hybrids, or non-paired probe nucleic acid molecules 50 are analyzed and used in detecting and quantifying the specific nucleic acid sequence of interest within the biological fluid 17.

As in the first embodiment of the test disc 40, the test disc 40 of the second embodiment is received into a cartridge's well 25 that has a depth sufficient to accommodate the biological fluid 17 and the disc 40, as seen in FIGS. 7, 9, 26A-26D.

Figure 26A:
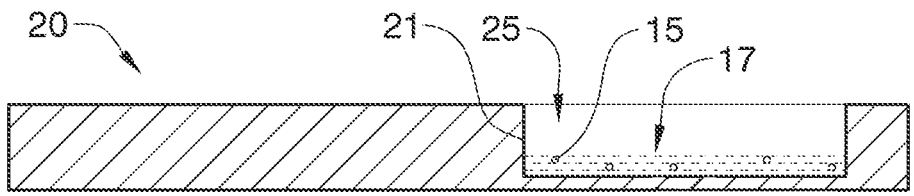
FIG. 26A is a cut view schematic of the cartridge (with the cut view taken along line—3, 4, 5, 6, 26—of FIG. 2) configured with a concave well, with a biological sample fluid (including virus with the target RNA of interest) introduced into the concave well in an embodiment of the present invention.
Figure 26B:
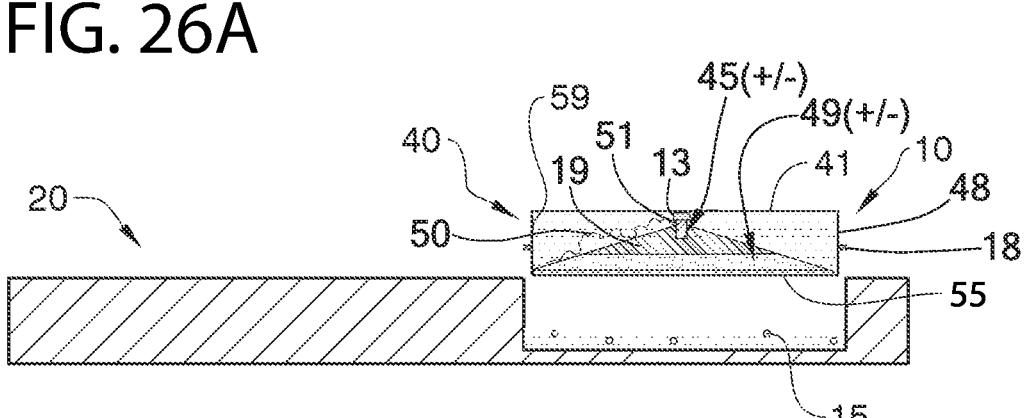
FIG. 26B is a cut view schematic of the cartridge of FIG. 26A with the biological sample fluid introduced into the concave well (serving as both a specimen-receiving aperture and a disc-receiving aperture) and with a test disc (enclosing one exemplary probe ss/pssNA molecule) in position to be moved into the well, which is shaped as a cylindrical depression.
Figure 26C:
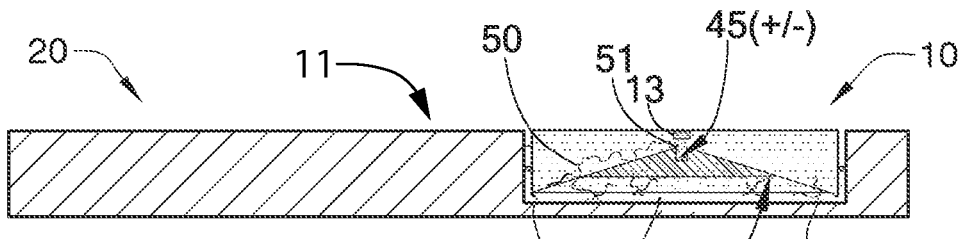
FIG. 26C is a cut view schematic of the cartridge of FIG. 26B with the bottom of test disc open to allow mixing of the reagent with the biological sample fluid, which opens the virus and unwinds the viral RNA in an embodiment of the present invention.
Figure 26D:
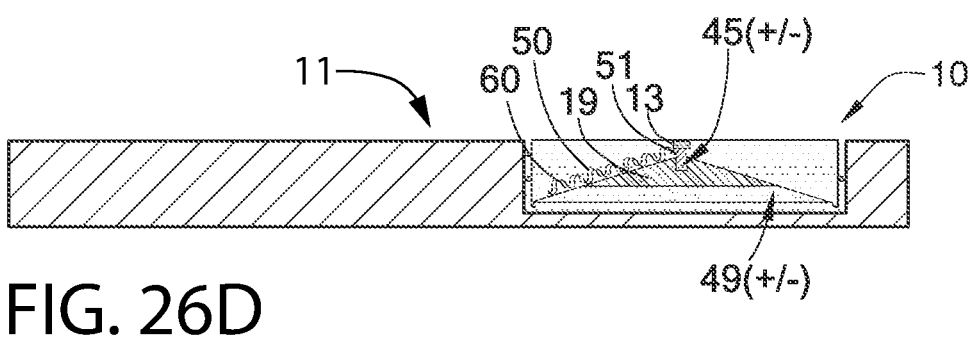
FIG. 26D is a cut view schematic of the cartridge of FIG. 26C with the bottom of the test disc open to allow the viral RNA present to hybridize with the exemplary single probe molecule in an embodiment of the present invention.
Figure 27:
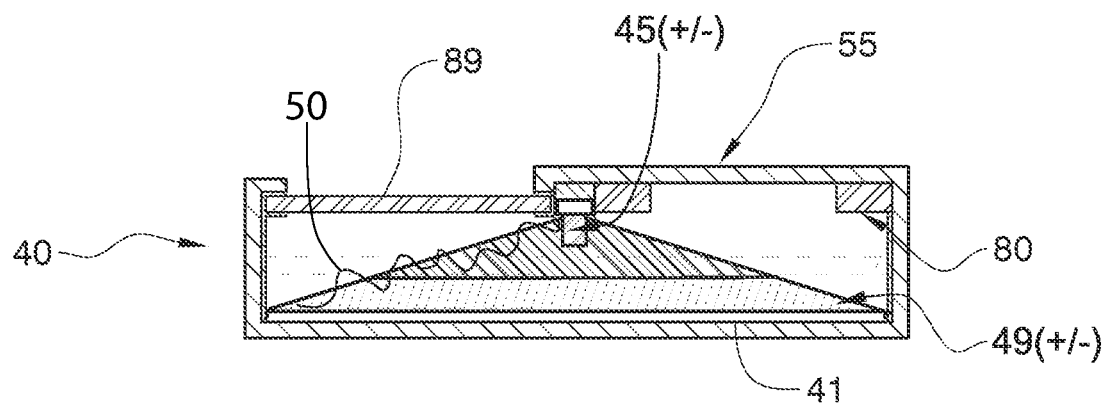
FIG. 27 is a cut view schematic taken along lines—8, 27—of FIG. 7 of the test disc with the two-part mechanical/structural opening feature in an embodiment of the present invention.

In an aspect of the invention, a central area at the bottom of the concave well 25 is preferably configured with an electrically conductive element 24. In this aspect, the disc 40 is installed in the well 25 in an inverted placement, as seen in FIG. 9 (which is the opposite of the orientation shown in FIGS. 26B-26D). FIG. 27 shows the disc 40 before inversion and installation in the well 25. Upon installation, the conductive element 24 provides electrical power to the central first conductor 45 of the disc 40. The power may be derived from the cartridge 20, from the electrical sensing subsystem 70, or from another suitable source. Thus, though the disc 40 is shown in FIGS. 26B-26D as inserted into the cartridge 20 with the narrow portion of the cone upwards, it may be preferred to install the disc 40 in an inverted disposition with the narrow portion of the cone downward. This inverted orientation and structure (as in FIG. 27) may allow the fluid easier access into the interior of the disc 40 for mixing, as well as affording advantages in providing electric current to the first electrode 45.

Steps in performing the rapid test are shown in FIGS. 26A-26D. These figures are schematics of cut views of the cartridge 20 with a test disc 40 (carrying probe 50) to be inserted within the cartridge well 25. These figures show the state in which the target virus 15 is contained within the sample biological fluid 17. Though only one probe ss/pssNA is shown for clarity of illustration, multiple probe ss/pssNA would be draped downwardly from the first electrode 45.

The technician obtains a test disc 40 and a corresponding test cartridge 20, with the test disc 40 carrying within it ss/pss probe nucleic acid molecules 50 that are at least partially complementary to the specific nucleic acid sequence of interest, the target ssNA molecule 60. As seen in FIG. 26A, the sample biological fluid 17 is obtained from the person being tested and introduced into concave well 25. The fluid 17 may be introduced in its native state, may be chemically pre-treated (such as a reagent being added), or may be mechanically pre-treated before being deposited into the well 25. Optionally, a reagent and/or other chemical treatment may be added to the well 25 to mix with the fluid 17.

The test disc 40 is then inserted into the cartridge well 25, as seen in FIG. 26B.

Containment of the test fluids during insertion may be facilitated by structural features (such as gasket 18) of the cartridge 20.

As seen in FIG. 26C, the test disc 40 is opened to allow the fluid 17 to mix with the contents of the test disc 40, which at least includes the probe nucleic acid molecules 50 (and may include the reagent solution). In an example, the bottom wall 55 of the test disc 40 may be fully or partially removed or opened. In another example, disc 40 is inserted in an inverted orientation, and the top wall 89 is opened, as shown in FIGS. 9, 11, and 27.

In an aspect of the invention, the reagent is not added to the concave well 25 before insertion of the test disc 40 but is instead carried within the disc 40. In another aspect of the invention, a portion of the reagent is added to the well 25 before insertion of the test disc 40 and another portion of the reagent is carried within the disc.

The fluid 17 is mixed with the reagent with the resulting sample-reagent solution washed over the probe nucleic acid molecules 50 within the test disc 40. The disc 40 may be inverted or agitated to increase mixing of the reagent-fluid solution with the probe nucleic acid molecules 50. The mixing process may include manual shaking, centrifuging (such as a vertical centrifuge), mechanical shaking by the electrical sensing subsystem 70 or a separate machine, or the like. The mixing process may also include heating the disc 40 to promote mixing via convection.

In another aspect of the invention the reagent may be contained in a separate compartment 30 of the disc 40 and may be allowed to mix with the sample fluid 17 before the resulting sample-reagent solution is introduced to the probe nucleic acid molecules 50. This two-compartment disc 40 may be designed in various ways, but in an example illustrated in FIGS. 6b-6E, the lower compartment is opened, such as by removing or opening the bottom floor, to allow the reagent to contact the virus within the fluid 17.

An electrical current is applied to the disc 40, such as by or through the cartridge 20. Preferably the electrical current is supplied by the electrical sensing subsystem 70 (FIGS. 18-19, 28-30) to minimize the cost of the cartridge 20 and disc 40.

After electrical current is applied to the disc 40, one or more electrical parameters are then read by the electrical sensing subsystem 70. The electrical parameter value obtained is compared to values in a predetermined array of conductivity/resistivity values to determine the presence and concentration of target ssRNA sequences. When the sample fluid 17 does not contain the virus with the target viral RNA, no hybridization occurs. Thus, when the electrical sensing subsystem 70 reads the electrical parameter, there is no change from the non-detection reference value of the electrical parameter. The detection circuit is in a first non-detection state when the target ssNA is absent.

In another aspect of the invention, the detection circuit is in a second partial-hybridization state, which presents different electrical parameters than the other states. In this state the target ssNA molecules are partially hybridized with the probe nucleic acid molecules 50.

FIGS. 26A-26D show the situation in which the biological fluid 17 does contain the virus 15 having the target RNA. When the reagent is mixed with the fluid 17, the virus is denatured, and the viral nucleic acid strands are unwound, as seen in FIG. 26C. In FIG. 26D, fragments of the viral nucleic acid have fully hybridized with the probe 50. When electrical current is applied to the disc 40 and the electrical parameters are read by the electrical sensing subsystem 70, the fully hybridized complex will have electrical parameters that correspond to a fully hybridized third state. For example, a fully hybridized state may comprise a conductivity value higher than the non-hybridized state reference value and higher than the partially hybridized state value, or may have a resistance lower than the other states. The electrical parameter result is compared to values in the predetermined array of conductivity values to determine the presence and concentration of target ssRNA. The detection circuit is in the third fully hybridized state when the target ssNA molecules are fully hybridized with the probe nucleic acid molecules 50.

As in the aspect of the first embodiment shown in FIGS. 10-13, in the second embodiment of the disc, the disc-receiving aperture need not equivalent to concave well 25, but the disc-receiving aperture may be instead disposed within a portion of the cartridge 20 that is disposed below the well 25.

Figure 28:
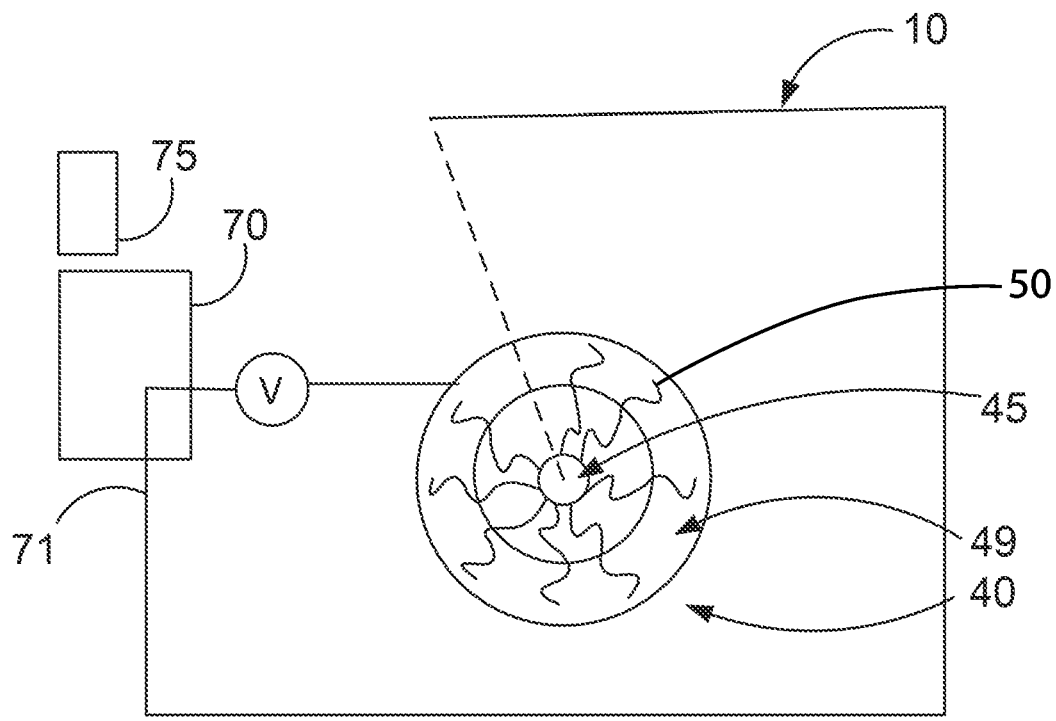
FIG. 28 is a schematic top view of an aspect of the invention in which the test system of the present invention obtains an electrical parameter reading from a single circuit.
Figure 29:
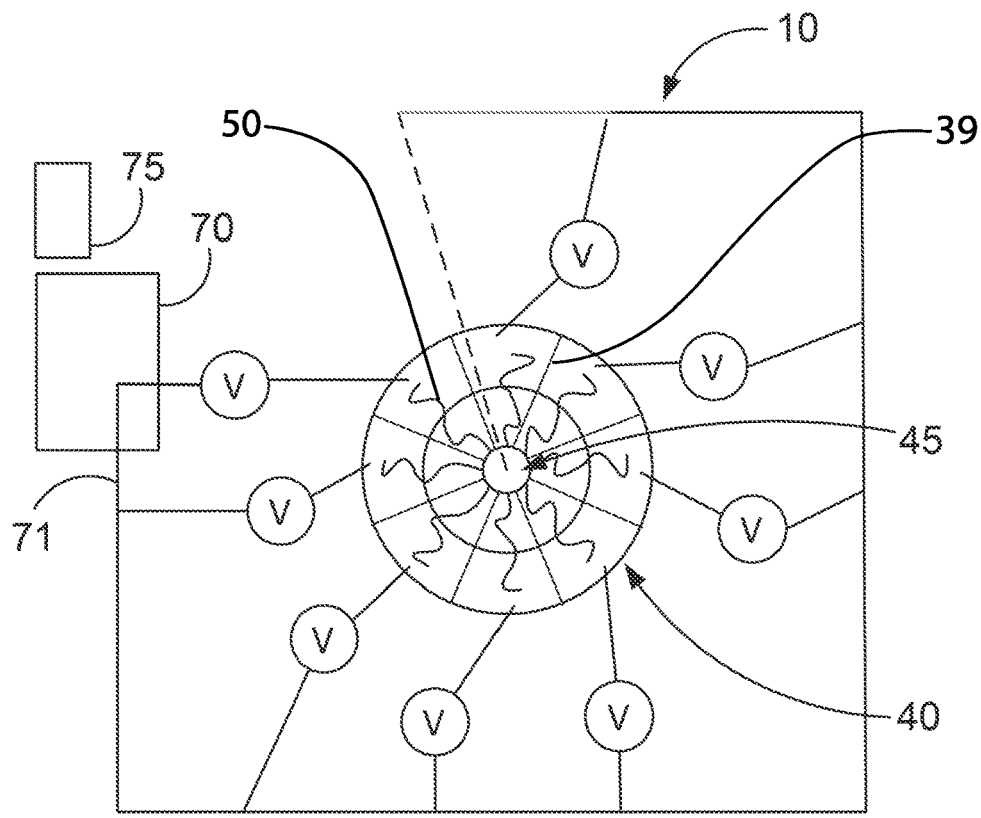
FIG. 29 is a schematic top view of an aspect of the invention in which the test system of the present invention obtains multiple electrical parameter readings with a reading from each of the electrically separated test disc segments.
Figure 30:
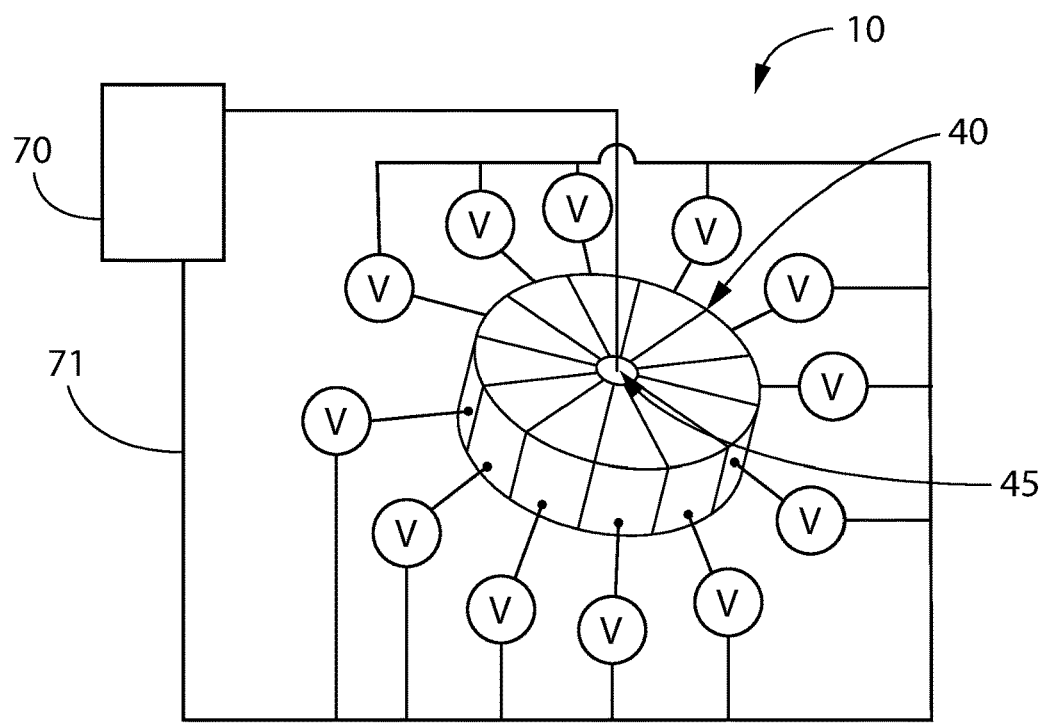
FIG. 30 is a schematic perspective view of an aspect of the invention in which the test system of the present invention obtains multiple electrical parameter readings with a reading from each of the electrically separated test disc segments.

FIGS. 28-29 are schematics that show that the electrical parameter readings by the electrical sensing subsystem 70 may comprise one or more reading circuits. The power and wiring for the reading circuit or circuits are preferably included within the cartridge and/or the electrical sensing subsystem 70. One or more electrical parameters (voltage, voltage drop, resistance, current, or the like) of the circuit are read by the electrical sensing subsystem 70.

FIG. 28 is a schematic view of an aspect of the invention in which the test system 10 of the present invention provides a single reading circuit between the first electrode 45 and the second electrode 49 of the electrical parameter. (No target ssNA molecules are shown in FIGS. 28-29.)

FIG. 29 is a schematic view of a further aspect of the invention in which the disc 40 additionally includes multiple electrically separated segments separated by interior dividers 39, with each segment being part of a separate circuit. Different types of probe nucleic acid molecules 50 may be disposed in each of the segments. Or every segment may contain the same type of probe nucleic acid molecules 50. The electrical sensing device 70 reads the multiple circuits, which are individually addressable. This embodiment of the invention provides advantages in redundancy (performing multiple tests at one time) and in providing the option for multi-target ssNA molecule detection, such as using one type of probe nucleic acid molecules in one segment, a second type of probe nucleic acid molecules in second segment, etc.

As seen in FIG. 29, the disc 40 is formed of multiple electrically separated segments with the heads 51 of a single row of probe nucleic acid molecules 50 attached to the center conductor 45 within a segment of the disc 40. And the tails 59 of that row of probes 50 attached to a single segment. Each segment may accommodate one or more rows of probes 50.

In one aspect of the invention, the probe nucleic acid molecules 50 comprise ssRNA molecules having a sequence that is complementary to a sequence of the target ssRNA molecules from the virus of interest. However, because ssRNA is relatively unstable and requires maintenance at low temperatures, this increases the cost of shipping and storage of tests including ssRNA. Therefore, in a further aspect of the invention, the probe nucleic acid molecules 50 comprise single strand or at least partially single-strand DNA (ss/pssDNA) molecules, with at least a portion of each probe ss/pssDNA molecule 50 designed to be complementary to the target ssRNA from the virus of interest. This reduces shipping and storage costs for the test discs 40, thus reducing the overall cost of the rapid test of the instant invention.

Combinations of these and other disclosed embodiments and aspects are within the scope of the invention.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A system for detection of a target nucleic acid molecule in a specimen, comprising:
a cartridge including a cartridge top portion, an opposing cartridge bottom portion, and a concave well disposed in said cartridge top portion; wherein said concave well comprises an open-top specimen-receiving aperture defined by a well bottom and well side walls, wherein said specimen-receiving aperture accommodates a volume of a specimen biological fluid potentially containing said target nucleic acid molecule; and
a test disc insertable into said concave well; said test disc comprising a first conductor, a second conductor electrically separated said first conductor, and probe nucleic acid molecules bridging a gap between said first conductor and said second conductor; wherein said probe nucleic acid molecules comprise at least partially single-stranded nucleic acid molecules; wherein said test disc is openable to introduce said specimen biological fluid to said probe nucleic acid molecules; and wherein, if said specimen biological fluid contains said target nucleic acid molecule hybridization occurs.

2. The system for detection of a target nucleic acid molecule in a specimen, as recited in claim 1, wherein said test disc further comprises a truncated cone construction comprising a cone truncated top portion and a cone base; wherein said first conductor is disposed at said cone truncated top portion; wherein said second conductor is disposed at said cone base; and wherein said truncated cone construction further comprises an intermediary portion disposed between, and electrically separating, said first conductor and said second conductor.

3. The system for detection of a target nucleic acid molecule in a specimen, as recited in claim 1, wherein said test disc further comprises disc side walls and a disc center area; wherein said first conductor is disposed at said disc center area; and wherein said second conductor comprises a cylindrical wall disposed inside of said disc side walls.

4. The system for detection of a target nucleic acid molecule in a specimen, as recited in claim 1, wherein said probe nucleic acid molecules are attached laxly between said first conductor and said second conductor.

5. The system for detection of a target nucleic acid molecule in a specimen, as recited in claim 1, wherein said test disc further comprises a reagent; wherein said test disc further comprises a reagent compartment that contains said reagent; and wherein said reagent compartment is openable to allow said reagent to mix with said specimen biological fluid.

6. The system for detection of a target nucleic acid molecule in a specimen, as recited in claim 5, wherein said test disc comprises a two-compartment test disc comprising said reagent compartment and a compartment containing said probe nucleic acid molecules.

7. The system for detection of a target nucleic acid molecule in a specimen, as recited in claim 5, wherein said specimen biological fluid comprises a viral agent containing said target nucleic acid; and wherein when said reagent is mixed with said specimen biological fluid, said viral agent is opened and said target nucleic acid is at least partially unwound to create single-strand nucleic acid.

8. The system for detection of a target nucleic acid molecule in a specimen, as recited in claim 1, wherein said open-top specimen-receiving aperture accommodates insertion of said test disc.

9. The system for detection of a target nucleic acid molecule in a specimen, as recited in claim 1, wherein said cartridge further comprises a disc-receiving aperture defined by an aperture roof, aperture side walls, an aperture back wall, an aperture floor, and an aperture side opening; wherein a portion of said disc-receiving aperture is disposed below said concave well; wherein said disc-receiving aperture accommodates insertion of said test disc; and wherein said concave well comprises a movable floor configured to move to allow said specimen biological fluid to feed downward.

10. The system for detection of a target nucleic acid molecule in a specimen, as recited in claim 1 further comprising a detection circuit for providing an indication of the presence or absence of said target nucleic acid molecule by measuring one or more electrical parameters; wherein said probe nucleic acid molecules are aligned in rows of probe nucleic acid molecules; and wherein said detection circuit provides an electrical reading from each of said rows of probe nucleic acid molecules or from groups of said rows of probe nucleic acid molecules.

11. The system for detection of a target nucleic acid molecule in a specimen, as recited in claim 1, further comprising:
a detection circuit for providing an indication of the presence or absence of said target nucleic acid molecule by measuring one or more electrical parameters; and
a signaling device for receiving and displaying one or more results from said detection circuit.

12. The system for detection of a target nucleic acid molecule in a specimen, as recited in claim 1, further comprising a disc holder for accommodating said test disc and multiple additional test discs; wherein said disc holder comprises a power source configured to supply current to said test disc and said multiple additional test discs when said test disc is installed within said disc holder with the current functional to maintain said probe nucleic acid molecules in a stretched configuration bridging said gap between said first conductor and said second conductor.

13. The system for detection of a target nucleic acid molecule in a specimen, as recited in claim 1, wherein said probe nucleic acid molecule comprises a central template strand of nucleic acid; a nucleic acid sequence (X) attached to a head-facing end of said central template strand of nucleic acid; and a nucleic acid sequence (Y) attached to a tail-facing end of said central template strand of nucleic acid; wherein said central template strand of nucleic acid is complementary to at least a portion of said target nucleic acid molecule.

* * * * *